(12) United States Patent
Murakami et al.

(10) Patent No.: US 10,188,797 B2
(45) Date of Patent: Jan. 29, 2019

(54) PHARMACEUTICAL INJECTION DEVICE

(71) Applicant: PHC Holdings Corporation, Minato-ku, Tokyo (JP)

(72) Inventors: Kenji Murakami, Ehime (JP); Mitsuteru Fujimoto, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 470 days.

(21) Appl. No.: 14/404,013

(22) PCT Filed: May 23, 2013

(86) PCT No.: PCT/JP2013/003295
§ 371 (c)(1),
(2) Date: Nov. 26, 2014

(87) PCT Pub. No.: WO2013/186997
PCT Pub. Date: Dec. 19, 2013

(65) Prior Publication Data
US 2015/0165121 A1 Jun. 18, 2015

(30) Foreign Application Priority Data
Jun. 13, 2012 (JP) .................................. 2012-133446

(51) Int. Cl.
*A61M 5/20* (2006.01)
*A61M 5/315* (2006.01)
(Continued)

(52) U.S. Cl.
CPC ................. *A61M 5/20* (2013.01); *A61M 5/24* (2013.01); *A61M 5/31575* (2013.01);
(Continued)

(58) Field of Classification Search
CPC .. A61M 5/20; A61M 5/24; A61M 2205/8206; A61M 5/31575;
(Continued)

(56) References Cited

U.S. PATENT DOCUMENTS 6,045,537 A 4/2000 Klitmose
6,186,982 B1 * 2/2001 Gross ................ A61M 5/14248
604/132

(Continued)

FOREIGN PATENT DOCUMENTS

EP 1640029 A1 3/2006
EP 2364739 A1 9/2011
(Continued)

OTHER PUBLICATIONS

The International Search Report of Int'l Appln. No. PCT/JP2013/003295 dated Aug. 27, 2013.
(Continued)

*Primary Examiner* — Bhisma Mehta
*Assistant Examiner* — Hamza Darb
(74) *Attorney, Agent, or Firm* — Wenderoth, Lind & Ponack L.L.P.

(57) ABSTRACT

This pharmaceutical injection device may be provided with a main body case, a pharmaceutical syringe mounting portion, a piston, a piston feed screw or the like, and a cover. At a first end, the main body case may have an injection needle mounting portion to which an injection needle is mounted. The pharmaceutical syringe mounting portion may be provided inside the main body case, and a pharmaceutical syringe may be mounted thereto. The piston may be provided movably with respect to the pharmaceutical syringe that is mounted to the pharmaceutical syringe mounting portion. The piston feed screw or the like drives the piston. The cover may be provided on the first end side of the main
(Continued)

body case and operates to open and close the injection needle mounting portion.

2 Claims, 29 Drawing Sheets

(51) Int. Cl.
    *A61M 5/24*     (2006.01)
    *A61M 5/31*     (2006.01)

(52) U.S. Cl.
    CPC ............ *A61M 2005/2414* (2013.01); *A61M 2005/3104* (2013.01); *A61M 2005/3125* (2013.01); *A61M 2205/18* (2013.01); *A61M 2205/52* (2013.01); *A61M 2205/581* (2013.01); *A61M 2205/8206* (2013.01)

(58) Field of Classification Search
    CPC .. A61M 2005/2414; A61M 2005/3104; A61M 2205/18; A61M 2005/3107; A61M 2205/52; A61M 2205/581; A61M 2005/3125; A61M 5/3271; A61M 5/3272
    See application file for complete search history.

(56) References Cited

U.S. PATENT DOCUMENTS

| | | | |
|---|---|---|---|
| 7,112,187 | B2 | 9/2006 | Karlsson |
| 7,922,699 | B2 | 4/2011 | Baba et al. |
| 8,206,351 | B2 | 6/2012 | Sugimoto et al. |
| 8,221,359 | B2 | 7/2012 | Kristensen et al. |
| 8,287,500 | B2 | 10/2012 | Baba et al. |
| 8,556,862 | B2 | 10/2013 | Cronenberg et al. |
| 2002/0004648 | A1* | 1/2002 | Larsen ................ A61M 5/326 604/195 |
| 2005/0090781 | A1 | 4/2005 | Baba et al. |
| 2005/0197650 | A1 | 9/2005 | Sugimoto et al. |
| 2005/0261634 | A1 | 11/2005 | Karlsson |
| 2007/0045288 | A1* | 3/2007 | Nelson ................ A61M 11/041 219/533 |
| 2007/0197968 | A1* | 8/2007 | Pongpairochana ..... A61M 5/20 604/131 |
| 2008/0306449 | A1 | 12/2008 | Kristensen et al. |
| 2009/0054832 | A1 | 2/2009 | Sugimoto et al. |
| 2009/0062777 | A1 | 3/2009 | Sugimoto et al. |
| 2011/0028906 | A1 | 2/2011 | Baba et al. |
| 2011/0033832 | A1 | 2/2011 | Baba et al. |
| 2011/0066131 | A1* | 3/2011 | Cabiri ................ A61M 5/14248 604/411 |
| 2011/0201999 | A1 | 8/2011 | Cronenberg et al. |
| 2011/0202013 | A1 | 8/2011 | Jeter et al. |
| 2011/0301534 | A1* | 12/2011 | Renz ................ A61M 5/2066 604/82 |

FOREIGN PATENT DOCUMENTS

| | | |
|---|---|---|
| JP | H11-505755 A | 5/1999 |
| JP | 2005-245852 A | 9/2005 |
| JP | 2006-500150 A | 1/2006 |
| JP | 2007-111301 A | 5/2007 |
| JP | 2008-514249 A | 5/2008 |
| JP | 2012-502764 A | 2/2012 |
| WO | 2000/41749 A1 | 7/2000 |
| WO | 2003/057286 A1 | 7/2003 |
| WO | 2012/003516 A2 | 1/2012 |

OTHER PUBLICATIONS

The Search Report from the corresponding European Patent Application No. 13804334.4 dated Jul. 1, 2015.

\* cited by examiner

FIG. 12B
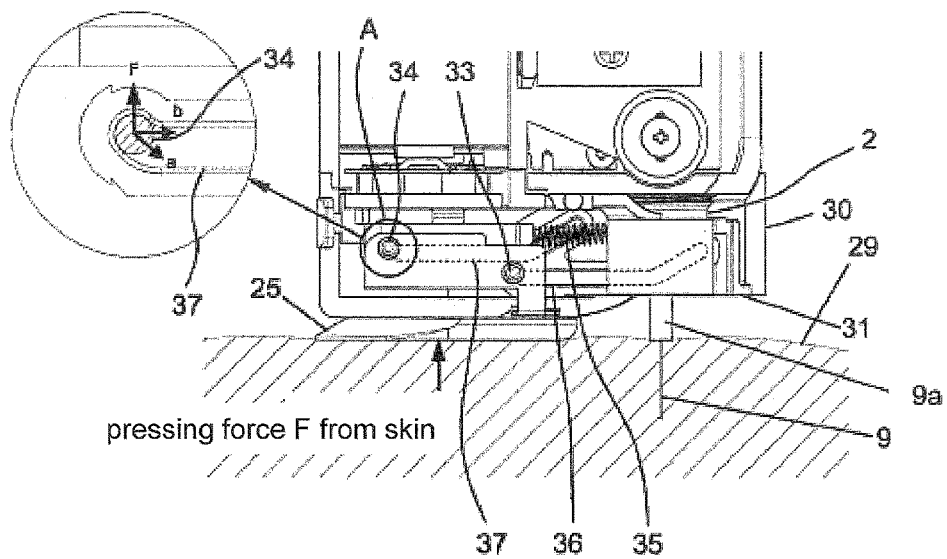
pressing force F from skin
FIG. 12A
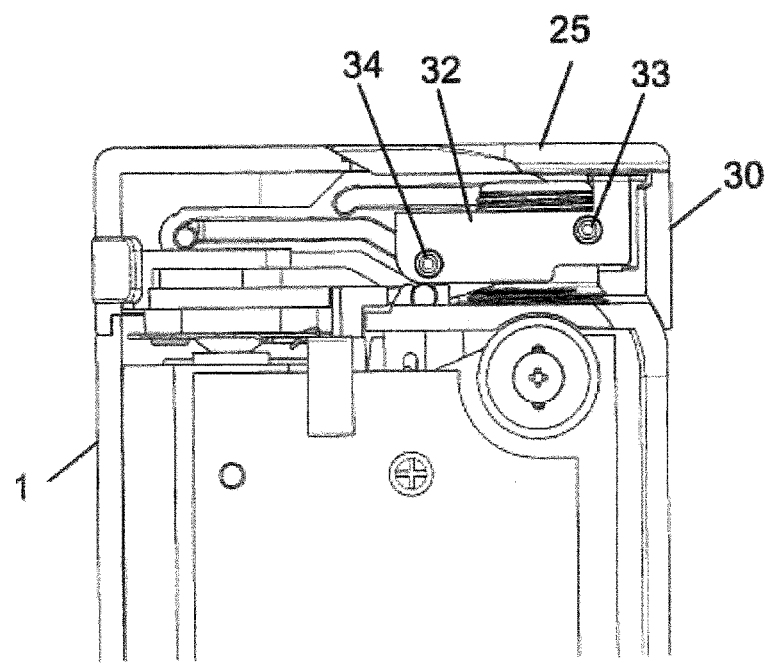
FIG. 13

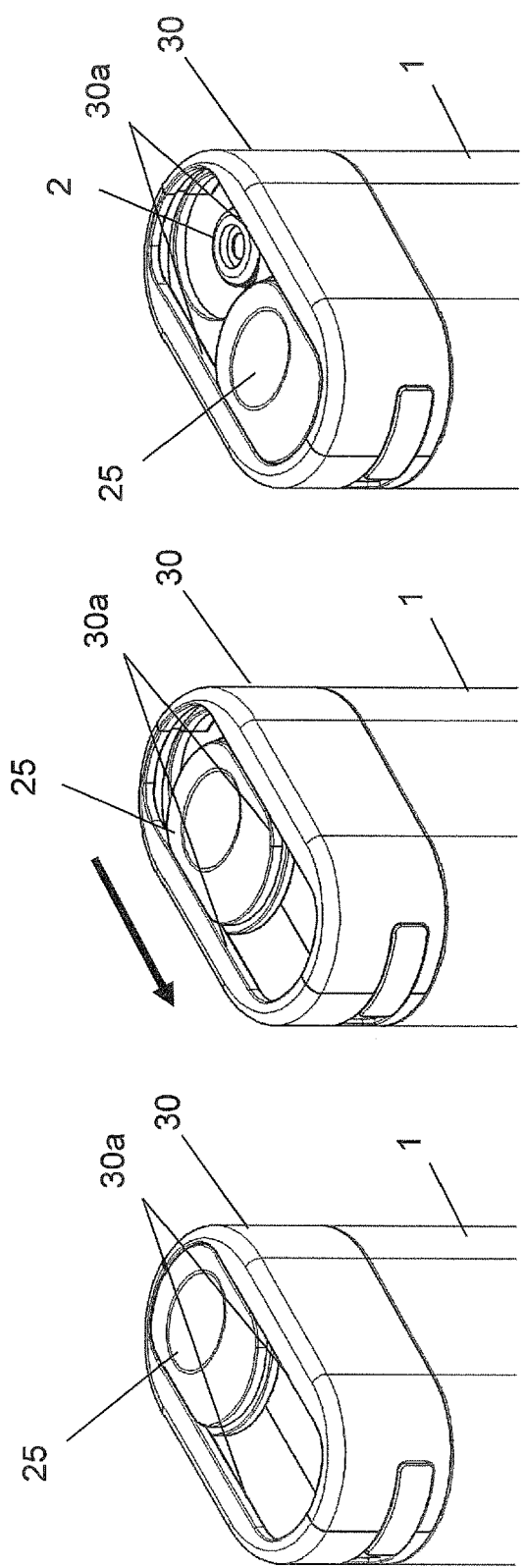

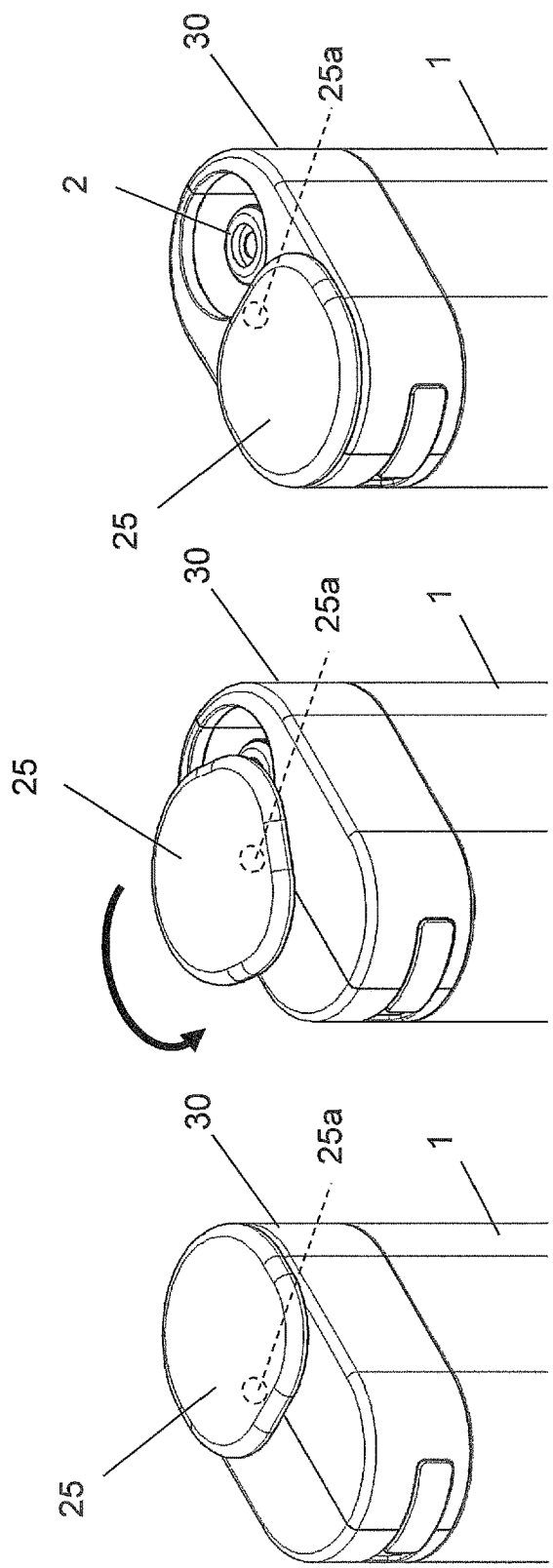

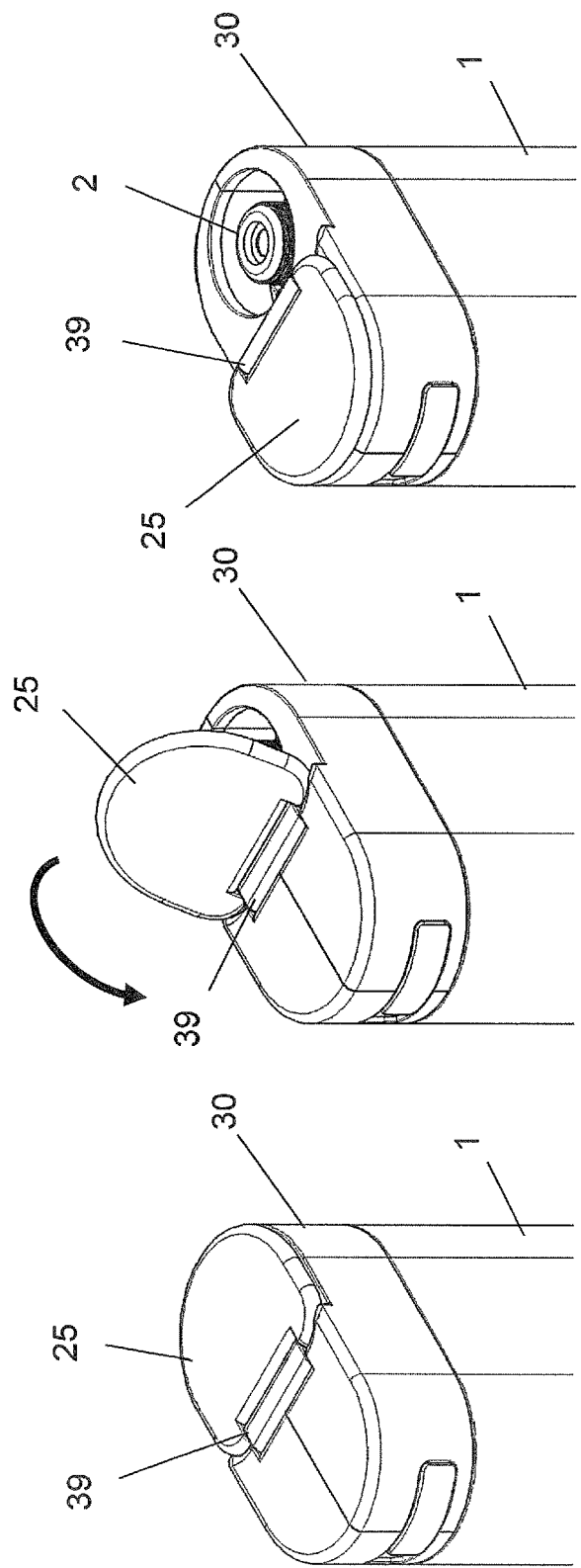

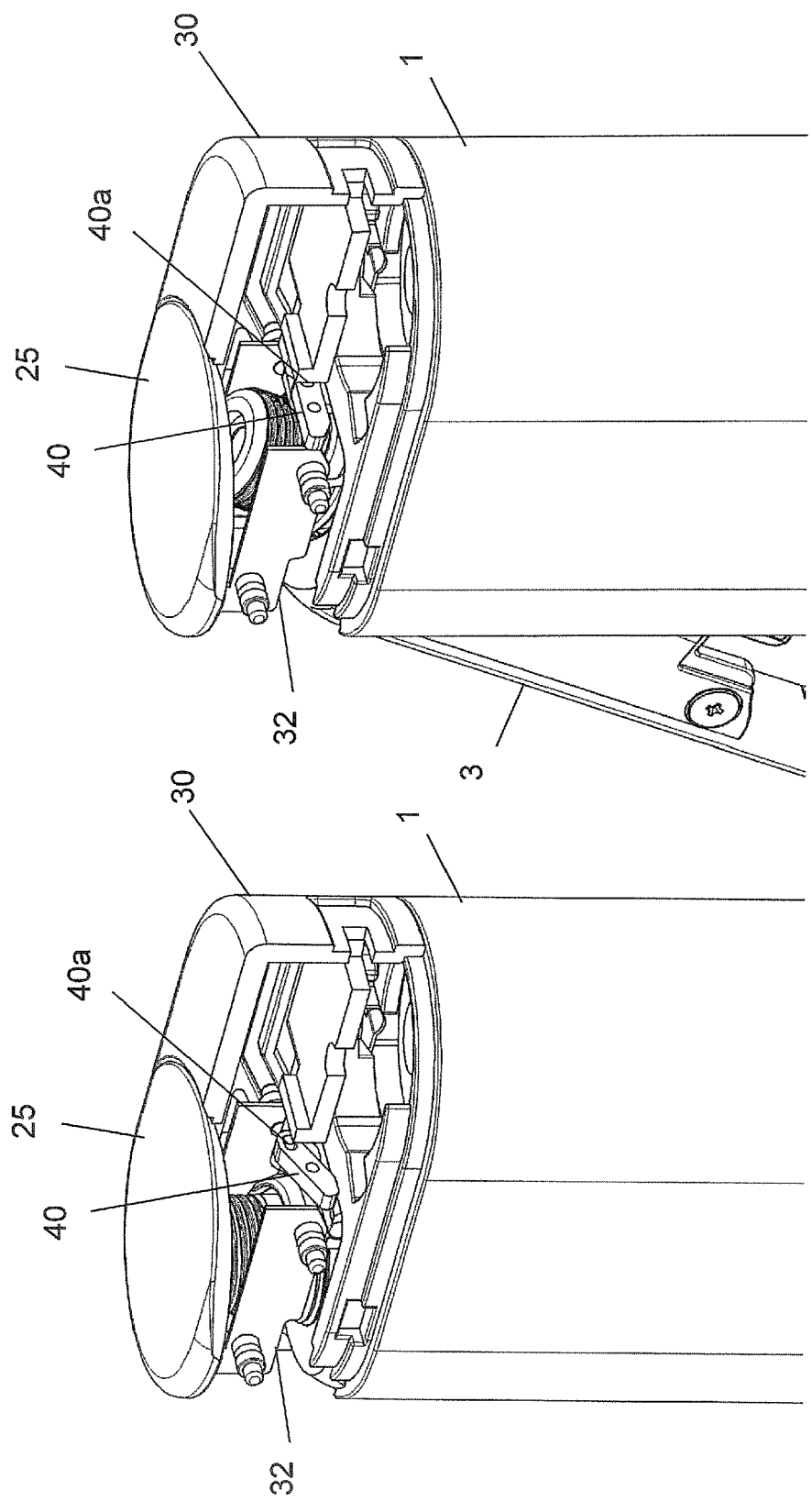

PHARMACEUTICAL INJECTION DEVICE

PRIORITY

This application is a U.S. National stage application of International Application PCT/JP2013/003295, with an international filing date of May 23, 2013, which claims priority to Japanese Patent Application No. 2012-133446 filed on Jun. 13, 2012. The entire disclosures of International Application PCT/JP2013/03295 and Japanese Patent Application No. 2012-133446 are hereby incorporated herein by reference.

TECHNICAL FIELD

The present invention relates to a pharmaceutical injection device for injecting a pharmaceutical into a human body, etc.

BACKGROUND ART

A pharmaceutical injection device typically comprises a main body case having an injection needle mounting portion at a first end, a pharmaceutical syringe mounting portion provided inside the main body case, a piston provided movably with respect to a pharmaceutical syringe mounted to the pharmaceutical syringe mounting portion, and a drive mechanism for driving the piston.

That is, with a conventional pharmaceutical injection device, first the pharmaceutical syringe is mounted to the pharmaceutical syringe mounting portion, and then the injection needle is mounted to the injection needle mounting portion. After this, the injection needle pierces the skin of the patient, and then a packing inside the pharmaceutical syringe is pushed by the piston through force from the drive mechanism, which injects the pharmaceutical inside the pharmaceutical syringe through the injection needle and into the patient's body.

Sometimes a cover that covers the injection needle mounting portion is removably mounted to the main body case in order to prevent the injection needle mounting portion from becoming dirty.

SUMMARY OF INVENTION

With the conventional example given above, the cover that covers the injection needle mounting portion is removably mounted to the main body case. This prevents the injection needle mounting portion from being soiled, but since the cover can be removed from the main body case, the cover may be lost, so this system can be inconvenient to use.

In view of this, it is an object of the present invention to provide a pharmaceutical injection device that is more convenient to use.

To achieve the stated objective, the pharmaceutical injection device of the present invention comprises a main body case, a pharmaceutical syringe mounting portion, a piston, a drive mechanism, and a cover. The main body case has an injection needle mounting portion at a first end to which an injection needle is mounted. The pharmaceutical syringe mounting portion is provided inside the main body case, and a pharmaceutical syringe is mounted thereto. The piston is provided movably with respect to the pharmaceutical syringe that is mounted to the pharmaceutical syringe mounting portion. The drive mechanism drives the piston. The cover covers the pharmaceutical syringe mounting portion in an opened and closed state wherein in the opened state, the injection needle mounting portion is exposed to the outside while the cover is still attached to the first end side of the main body case.

Consequently, the cover is provided on the first end side of the main body case in an openable and closeable state so as to cover the injection needle mounting portion. That is, since the cover is always mounted to the main body case, it will not be lost, thus making the device more convenient to use.

BRIEF DESCRIPTION OF THE DRAWINGS

FIGS. 2A and 2B are oblique views of the pharmaceutical injection device in which FIGS. 1A and 1B are flipped upside-down;

FIG. 12A is a detailed cross-sectional view of the pharmaceutical injection device in FIGS. 1A and 1B, and FIG. 12B is an enlarged detail view of the A portion in FIG. 12A;

FIG. 13 is a detailed cross-sectional view of the pharmaceutical injection device in FIG. 1A;

FIGS. 32A to 32C are oblique views of the configuration of the pharmaceutical injection device pertaining to another embodiment of the present invention;

FIGS. 33A to 33C are oblique views of the configuration of the main components of the pharmaceutical injection device pertaining to yet another embodiment of the present invention;

FIGS. 35A to 35C are oblique views of the configuration of the main components of the pharmaceutical injection device pertaining to yet another embodiment of the present invention; and FIGS. 36A to 36B are oblique views of the configuration of the main components of the pharmaceutical injection device pertaining to yet another embodiment of the present invention.

DETAILED DESCRIPTION

The pharmaceutical injection device pertaining to an embodiment of the present invention will now be described through reference to the appended drawings.

As shown in FIGS. 1A to 3, the pharmaceutical injection device in this embodiment comprises a columnar main body case 1, an injection needle mounting portion 2 provided on the first end side thereof (the piercing side), and a pharmaceutical syringe mounting portion 3 provided inside the main body case 1.

Figure 1A:
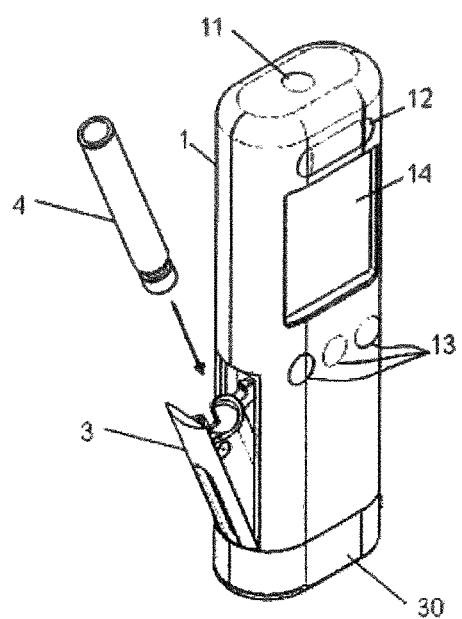
FIGS. 1A and 1B are oblique views of the pharmaceutical injection device pertaining to an embodiment of the present invention.
Figure 1B:
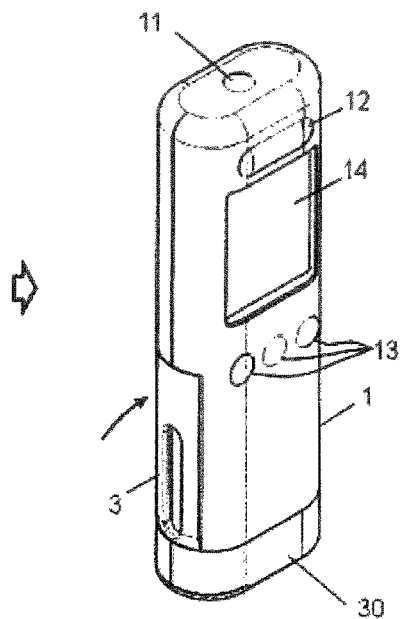

As shown in FIGS. 1A and 1B, the pharmaceutical syringe mounting portion 3 can stick out from the main body case 1, and as shown in FIG. 1A, a pharmaceutical syringe 4 is mounted to it in a state in which it has been pulled out from the main body case 1. After this, as shown in FIG. 1B, the pharmaceutical syringe mounting portion 3 is pushed into the main body case 1, so that the pharmaceutical syringe 4 is disposed at a specific position within the main body case 1 as shown in FIG. 3.

Figure 3:
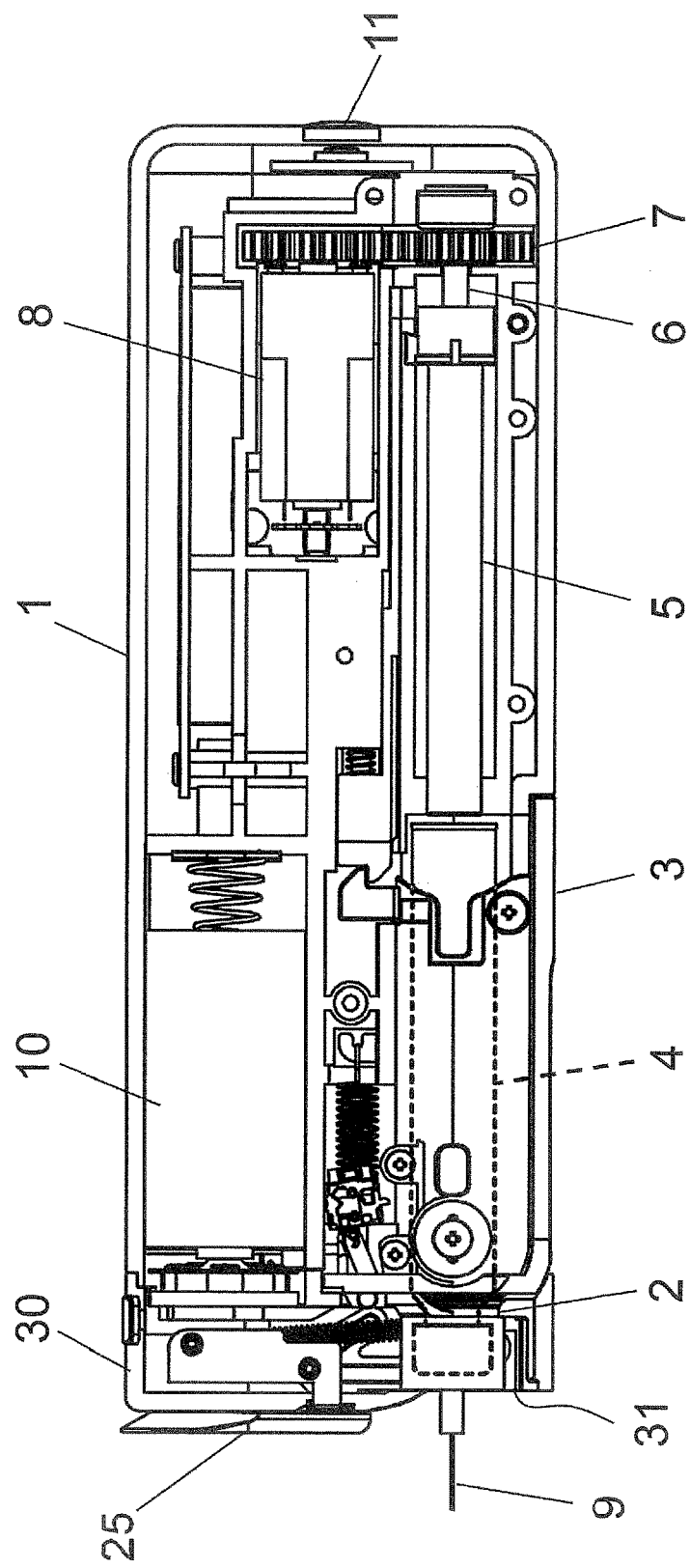
FIG. 3 is a cross-sectional view of the pharmaceutical injection device in FIG. 1B.

In the state shown in FIG. 3, a piston 5 is disposed in a state of being movable with respect to the pharmaceutical syringe 4 mounted inside the pharmaceutical syringe mounting portion 3.

That is, a motor (drive mechanism) 8 is linked to the piston 5 via a piston feed screw (drive mechanism) 6 and a gear (drive mechanism) 7. Therefore, when the motor 8 is actuated, the piston 5 is pushed to the pharmaceutical syringe mounting portion 3 side via the gear 7 and the piston feed screw 6. This allows the pharmaceutical inside the pharmaceutical syringe 4 to be injected into a patient's body, etc. (discussed in detail below).

The pharmaceutical syringe 4 is usually in the form of a circular cylinder. A gasket (not shown) that is pushed in by the piston 5 is disposed in the interior on the rear end side (the piston 5 side) in the piercing direction.

Also, a packing (not shown), at which the rear end side (the piston 5 side) of an injection needle 9 is pushed into, is disposed on the distal end side (the first end side) of the pharmaceutical syringe 4.

Figure 2A:
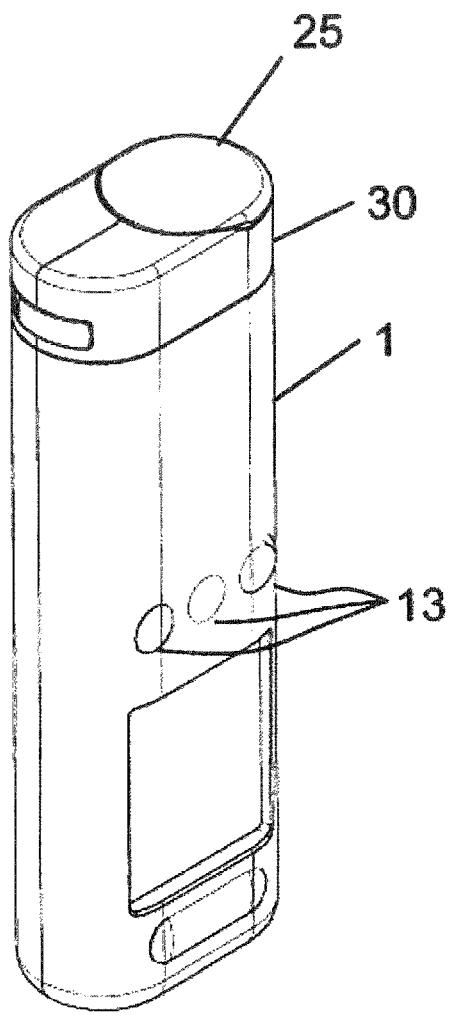

In this embodiment, as shown in FIGS. 2A to 3, the distal end side (the opposite side from the piston 5) of the pharmaceutical syringe 4 becomes the injection needle mounting portion 2. When the injection needle 9 is mounted to the injection needle mounting portion 2, the pharmaceutical in the pharmaceutical syringe 4 is injected through the injection needle 9 and into the body.

The battery 10 shown in FIG. 3 is provided to supply power to the various components.

Furthermore, a power button 11, a pharmaceutical injection button 12, a setting button 13 for setting pharmaceutical injection quantities and so forth, and a display section 14 that displays the operating state and so forth are provided towards the front of the main body case 1 (see FIGS. 1A, 1B, and FIGS. 2A, 2B).

Figure 4:
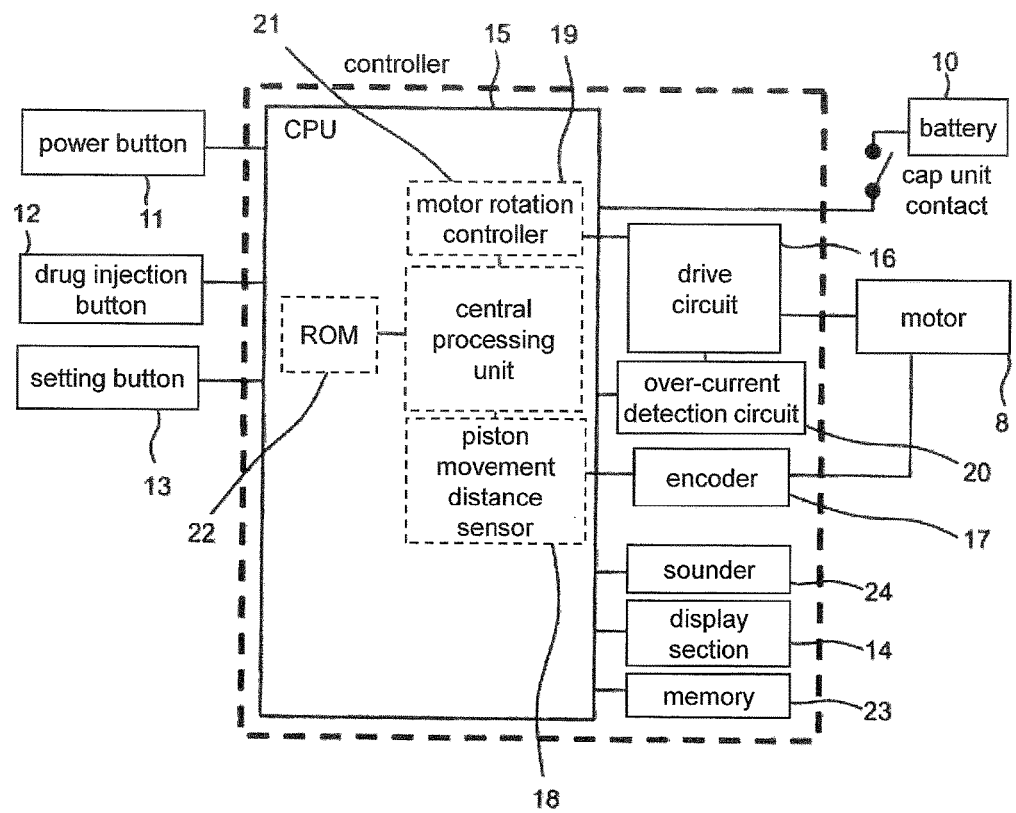
FIG. 4 is a control block diagram of the pharmaceutical injection device in FIG. 1B.

FIG. 4 shows the control blocks of this pharmaceutical injection device.

The battery 10, the power button 11, the pharmaceutical injection button 12, the setting button 13, and the display section 14 are connected to a controller 15.

The controller 15 is connected to the motor 8 via a drive circuit 16. Consequently, the amount of rotation of the motor 8, that is, the amount the piston 5 is pushed in, is sensed by an encoder 17 and a piston movement distance sensor 18.

The rotational control of the motor 8 is performed by a motor rotation controller 19, via the drive circuit 16. Over-current in the motor 8 is detected by an over-current detection circuit 20. Thus, the drive of the motor 8 is quickly stopped when an abnormality due to over-current is detected.

A central processing unit 21 and a ROM 22 containing programs are provided inside the controller 15. The controller 15 is also connected to a memory 23 that stores operational states, setting data, injection history, and so forth, and a sounder 24 that emits operating sounds, warning sounds, audio output, and so forth.

Now that the basic configuration of this embodiment has been understood from the above description, the main characteristics of this embodiment will be described.

Figure 2B:
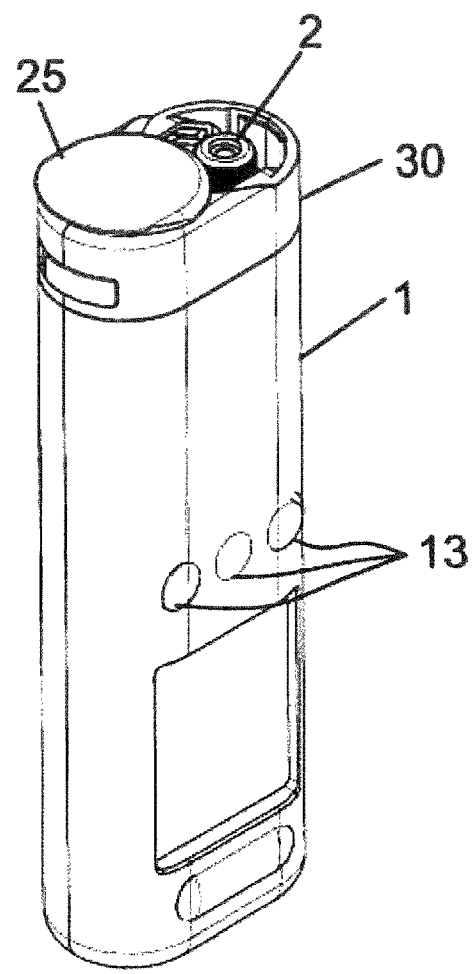

As shown in FIGS. 2A and 2B, in this embodiment the injection needle mounting portion 2 (also serves as the distal end side of the pharmaceutical syringe 4) is provided on the first end side of the main body case 1. The injection needle mounting portion 2 is covered by a cover 25 mounted to the main body case 1 in a state of being openable and closeable.

That is, when the injection needle 9 is mounted, the cover 25 is opened (see FIG. 2B), and in this state, as shown in FIGS. 5 to 11, the injection needle 9 is mounted to the injection needle mounting portion 2.

Figure 5:
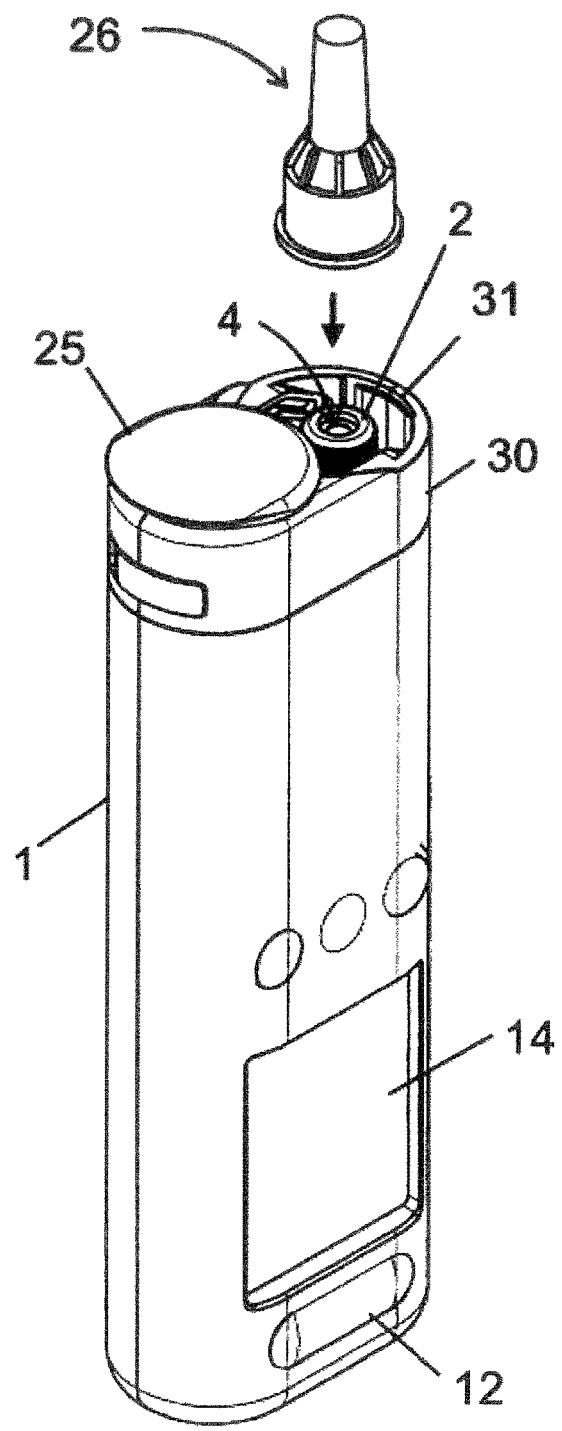
FIG. 5 is an oblique view of the usage state of the pharmaceutical injection device in FIG. 1B.
Figure 6:
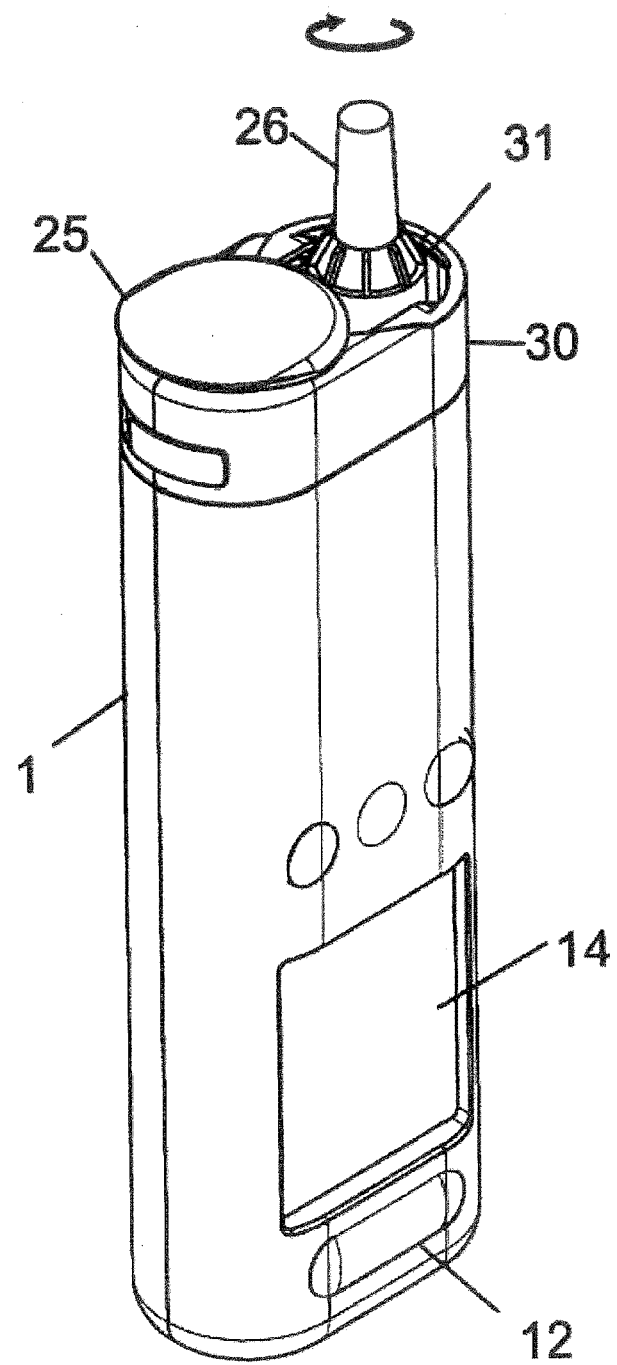
FIG. 6 is an oblique view of the usage state of the pharmaceutical injection device in FIG. 1B.

First, as shown in FIG. 5, the cover 25 is opened, and then, as shown in FIG. 6, a needle unit 26 is threaded into the injection needle mounting portion 2 (which also serves as the distal end side of the pharmaceutical syringe 4).

Figure 7:
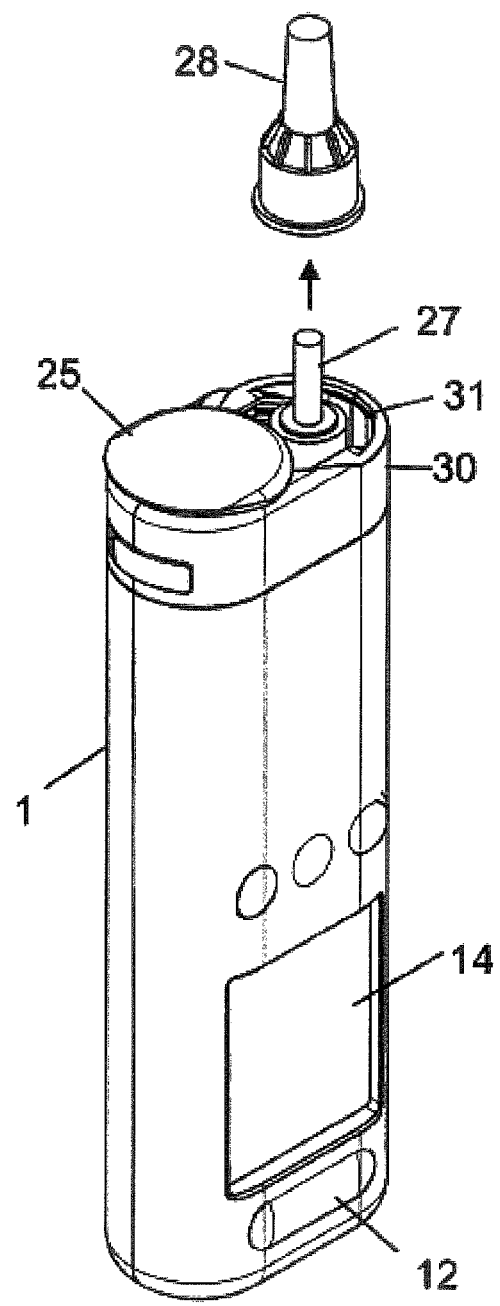
FIG. 7 is an oblique view of the usage state of the pharmaceutical injection device in FIG. 1B.
Figure 8:
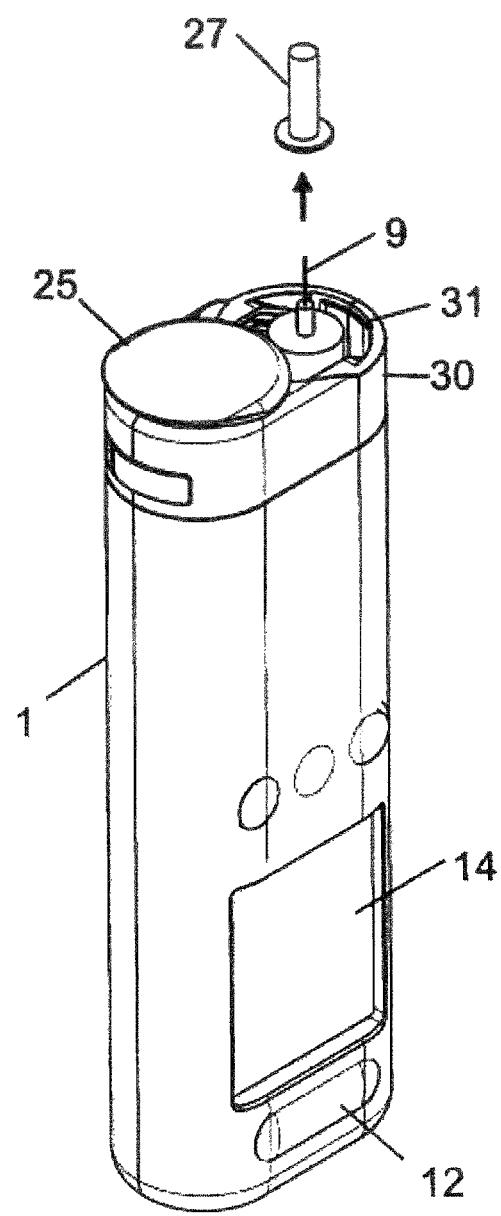
FIG. 8 is an oblique view of the usage state of the pharmaceutical injection device in FIG. 1B.
Figure 9:
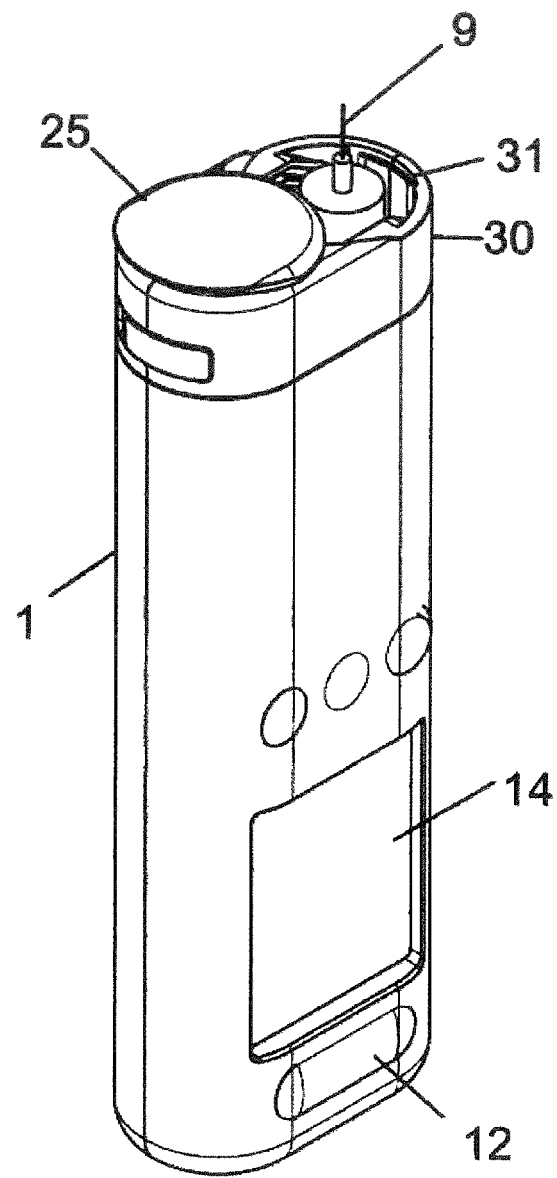
FIG. 9 is an oblique view of the usage state of the pharmaceutical injection device in FIG. 1B.
Figure 10:
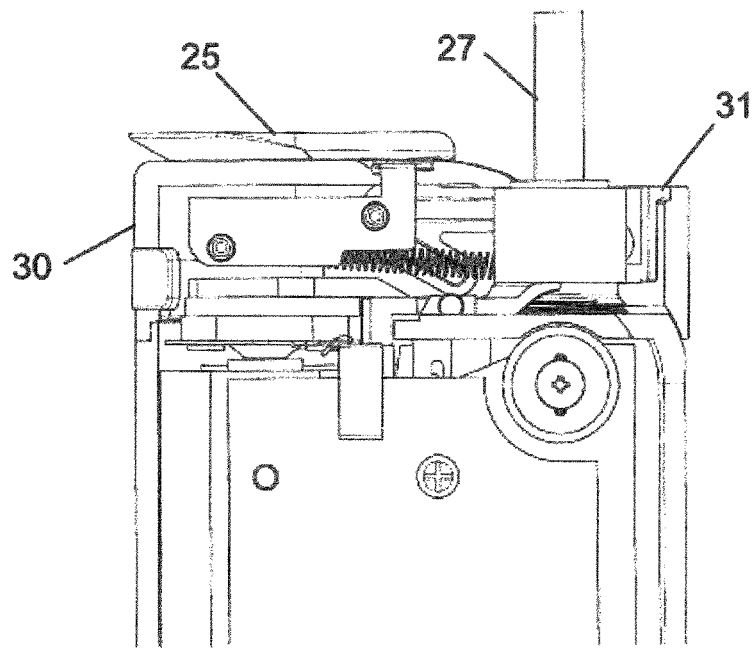
FIG. 10 is a detailed cross-sectional view of the pharmaceutical injection device in FIG. 1B.
Figure 11:
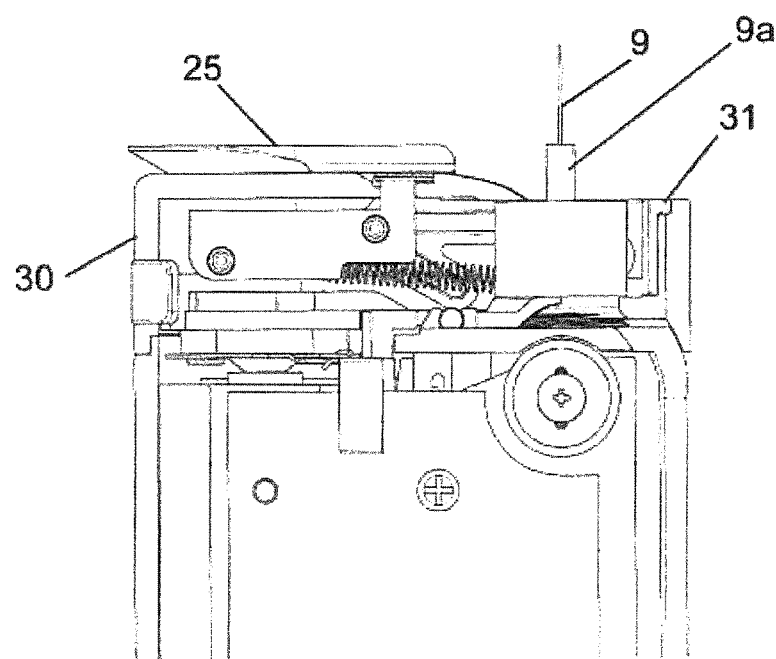
FIG. 11 is a detailed cross-sectional view of the pharmaceutical injection device in FIG. 1B.
Figure 14:
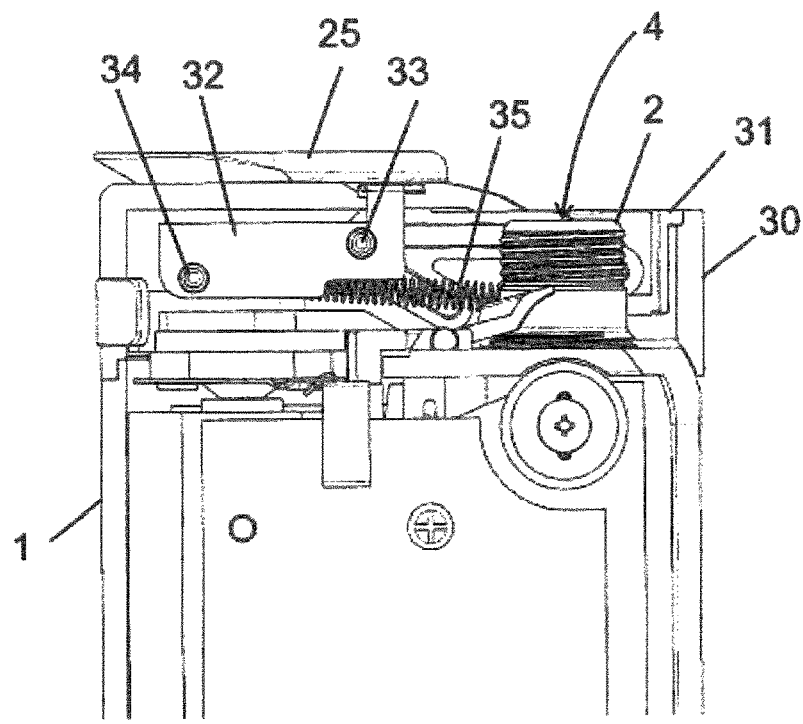
FIG. 14 is a detailed cross-sectional view of the pharmaceutical injection device in FIG. 1A.

As shown in FIGS. 5 to 11, the needle unit 26 is made up of the injection needle 9, a needle cap 27 that covers the injection needle 9, and a needle cover 28 on the outside of the needle cap 27. Therefore, as shown in FIG. 6, after the needle unit 26 has been threaded into the injection needle mounting portion 2 (also serves as the distal end side of the pharmaceutical syringe 4), as shown in FIG. 7, just the needle cover 28 is pulled off. Next, as shown in FIG. 8, the needle cap 27 is pulled off as shown in FIG. 8 from the state in FIG. 10. This exposes the injection needle 9 as shown in FIGS. 9 and 11.

A state in which the injection needle 9 is exposed is shown in FIG. 3, and in this state, the injection needle 9 is stuck into the skin 29 of the patient as shown in FIGS. 12A and 12B.

At this point, in this embodiment, the outer surface of the cover 25 is the skin contact face at the outer peripheral position of the injection needle mounting portion 2.

That is, the injection needle 9 can be pushed by the proper amount (the proper depth in this case) into the skin 29 as long as the cover 25 is pressed far enough to hit the skin 29.

A stepped part 9a of the injection needle 9 is formed on the rear side of the injection needle 9 in the piercing direction, in a larger diameter than the injection needle 9. The distal end face of the stepped part 9a on the injection needle 9 side is substantially the same height as the front of the cover 25 (see FIG. 11). Accordingly, as long as the cover 25 is pressed against the skin 29, the injection needle 9 can be pushed the proper amount into the skin 29 (see FIGS. 12A and 12B).

Therefore, if the pharmaceutical injection button 12 is pressed in this state, the motor 8 is actuated, and the piston 5 is pushed to the pharmaceutical syringe mounting portion 3 side via the gear 7 and the piston feed screw 6. This allows the pharmaceutical inside the pharmaceutical syringe 4 to be injected into the patient via the injection needle 9.

Next, the cover 25, which can be opened and closed while still mounted to the main body case 1 so that the injection needle mounting portion 2 can be exposed to the outside, will be described in detail through reference to FIGS. 12A to 15 and FIGS. 28 and 29.

Figure 28:
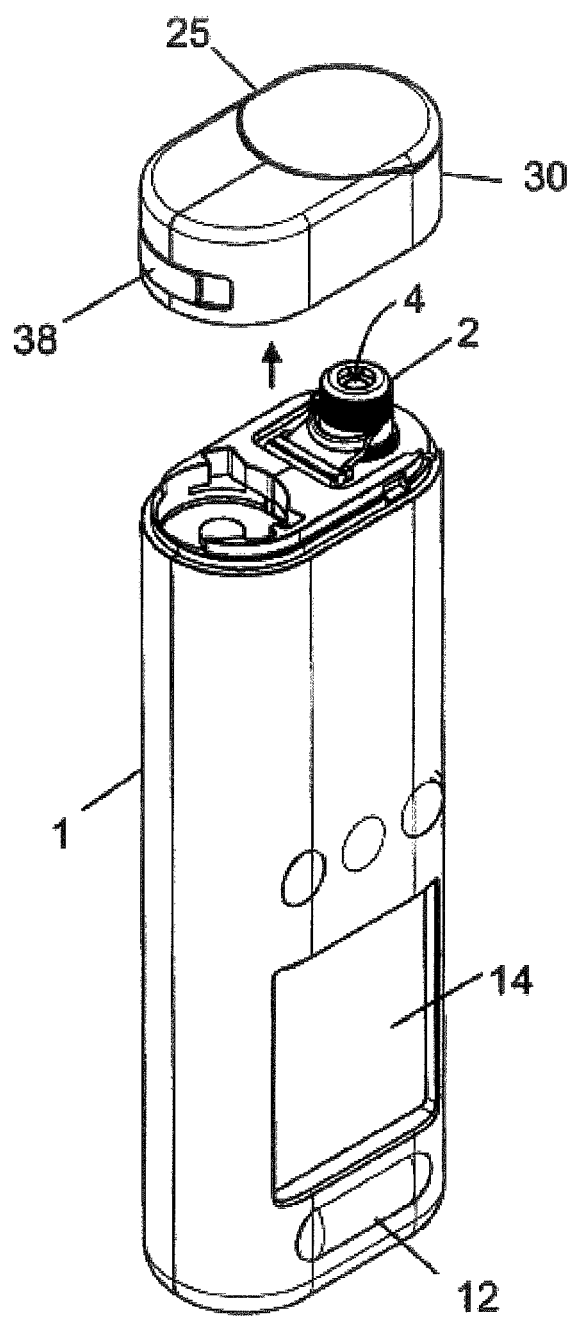
FIG. 28 is an oblique view of the usage state of the pharmaceutical injection device in FIG. 1A.
Figure 29:
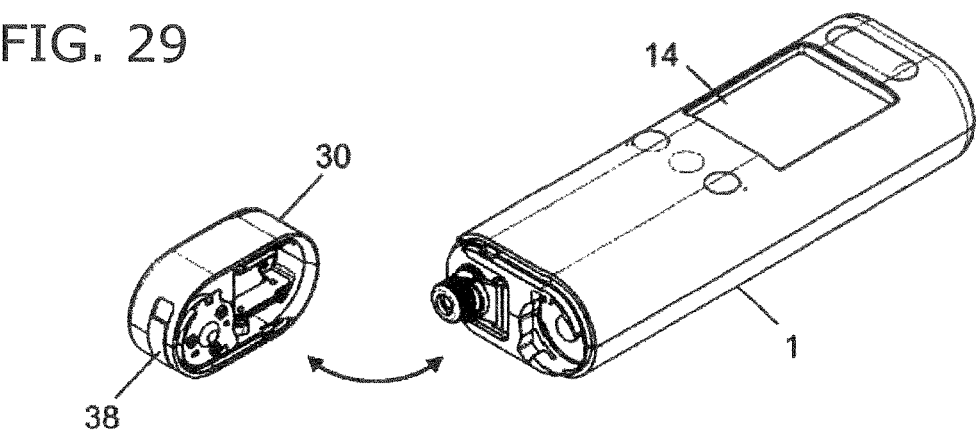
FIG. 29 is an oblique view of the usage state of the pharmaceutical injection device in FIG. 1A.

In this embodiment, a cap 30 is removably mounted as shown in FIGS. 28 and 29 on the first end side (the piercing direction side) of the main body case 1. As shown in FIG. 5, etc., the cap 30 is provided with an opening 31 that exposes the injection needle mounting portion 2.

The cover 25 is disposed so as to be capable of being opened and closed with respect to the opening 31. An opening and closing mechanism for opening and closing the cover 25 with respect to the opening 31 is provided inside the cap 30.

Figure 25:
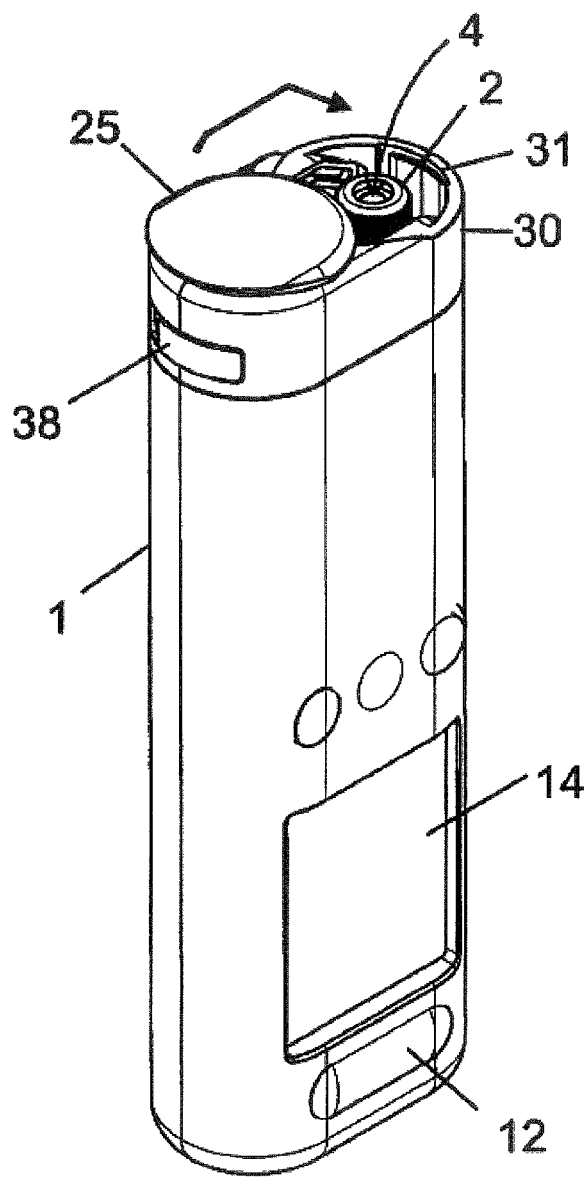
FIG. 25 is an oblique view of the usage state of the pharmaceutical injection device in FIG. 1A.
Figure 26:
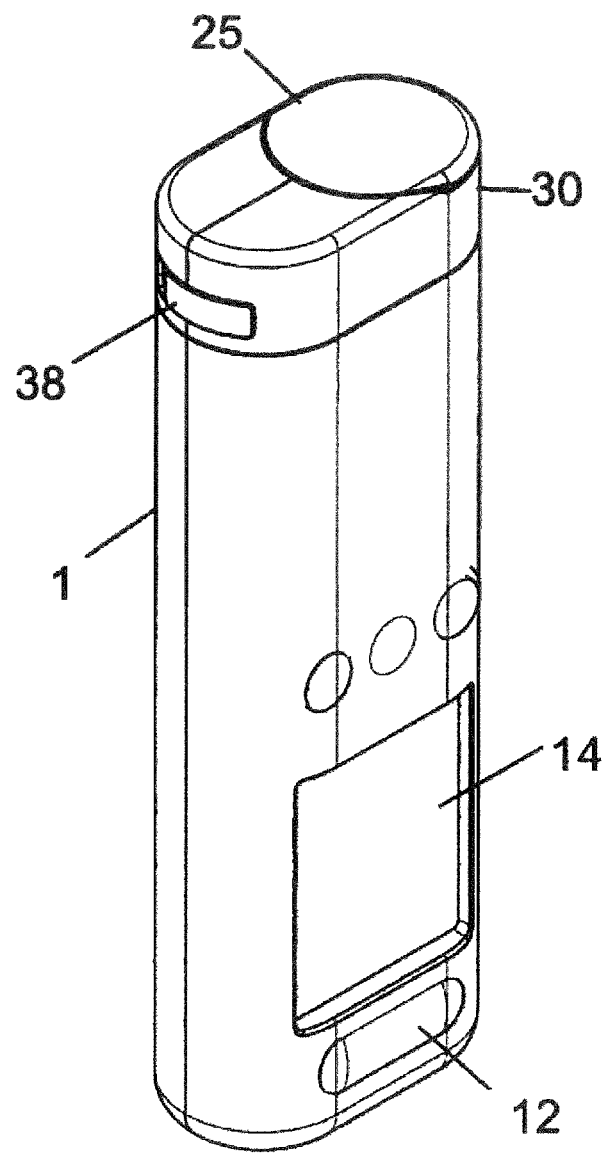
FIG. 26 is an oblique view of the usage state of the pharmaceutical injection device in FIG. 1A.
Figure 27:
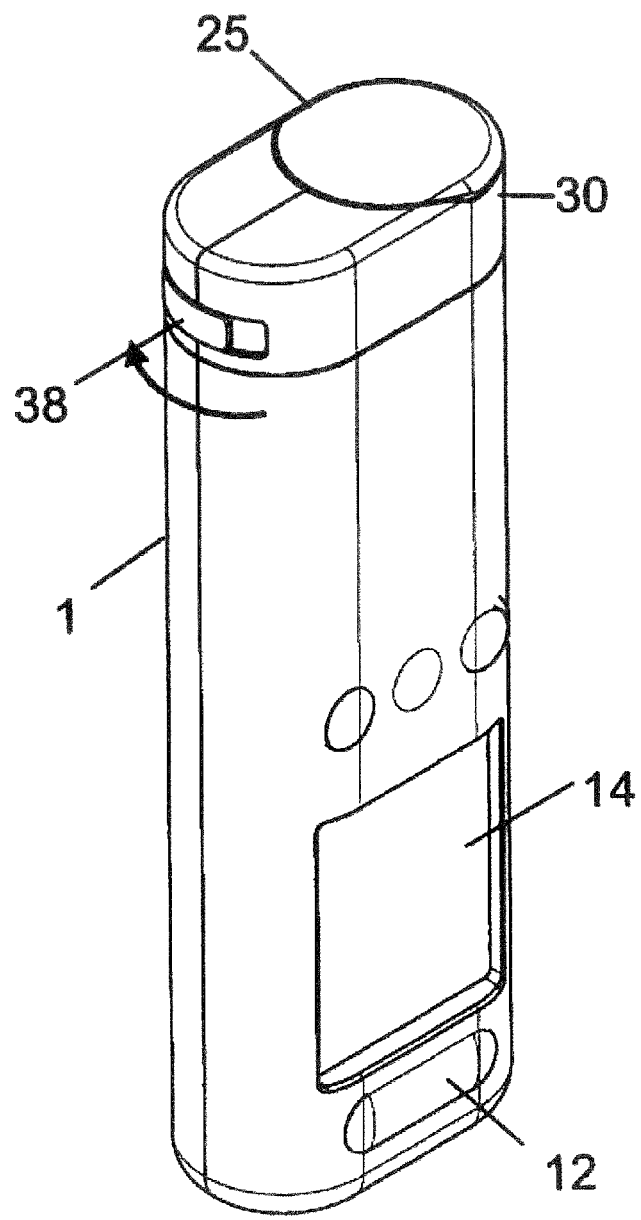
FIG. 27 is an oblique view of the usage state of the pharmaceutical injection device in FIG. 1A.

That is, the cap 30 is in the form of a cylinder having an upper face, and the above-mentioned opening 31, which is elliptical, is formed in this upper face (see FIGS. 5, 25, etc.).

Figure 18:
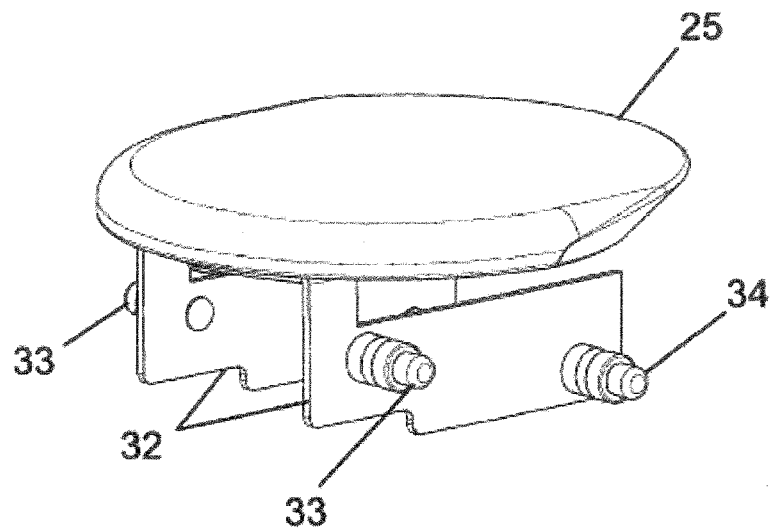
FIG. 18 is a detailed oblique view of the pharmaceutical injection device in FIG. 1A.
Figure 19:
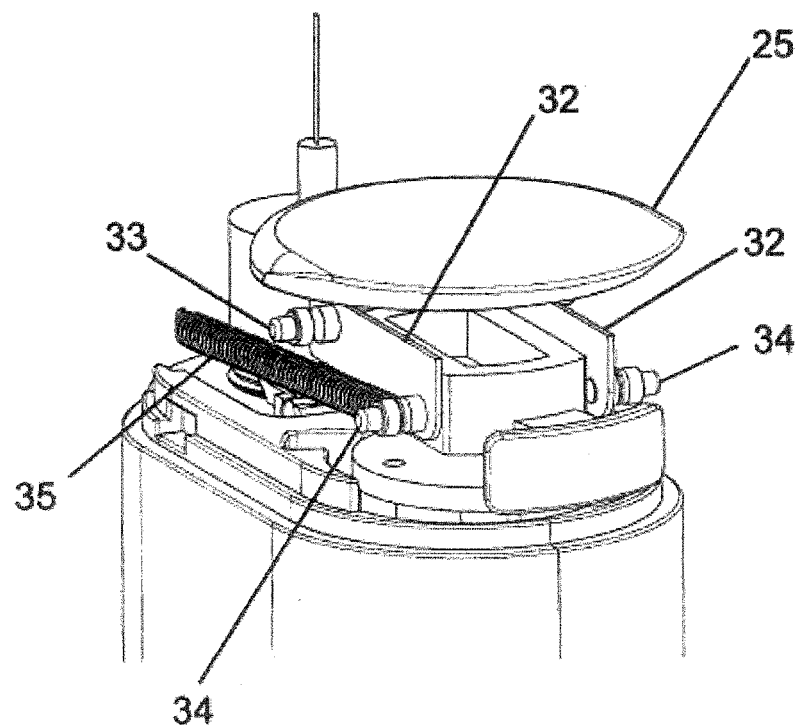
FIG. 19 is a detailed oblique view of the pharmaceutical injection device in FIG. 1A.

The cover 25 that covers the opening 31 in a state of being openable and closeable is in the form of an elliptical plate. As shown in FIG. 18, two substantially L-shaped arms 32 formed from spring material are provided to the rear side of the cover 25 (the inner side of the cap 30).

The substantially L-shaped arms 32 are disposed in parallel at a specific spacing along the opening and closing direction of the cover 25, and substantially L-shaped first ends are each fixed to the rear side of the cover 25.

Slide pins 33 and 34 are provided substantially perpendicular to and on the face of the middle portion of the substantially L-shaped arms 32. They can also be provided on the face on the second end side (the opposite side from the first end).

Figure 15:
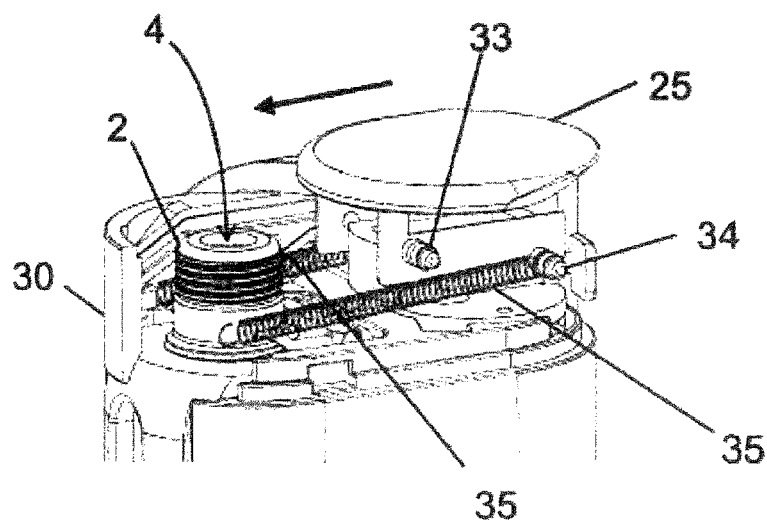
FIG. 15 is an oblique view of the pharmaceutical injection device in FIG. 1A.

The slide pins 34 are provided closer to the main body case 1 side than the slide pins 33. As shown in FIG. 15, the first end side of slide springs 35 is mounted to the slide pins 34. Meanwhile, the second end side of the slide springs 35 is mounted to engagement components (not shown) provided near the injection needle mounting portion 2 on the inside of the cap 30.

With the configuration shown in FIG. 15, since two substantially L-shaped arms 32 are provided in parallel, two of the slide springs 35 are also provided in parallel.

That is, the cover 25 is biased by the slide springs 35 in the closing direction.

Figure 16:
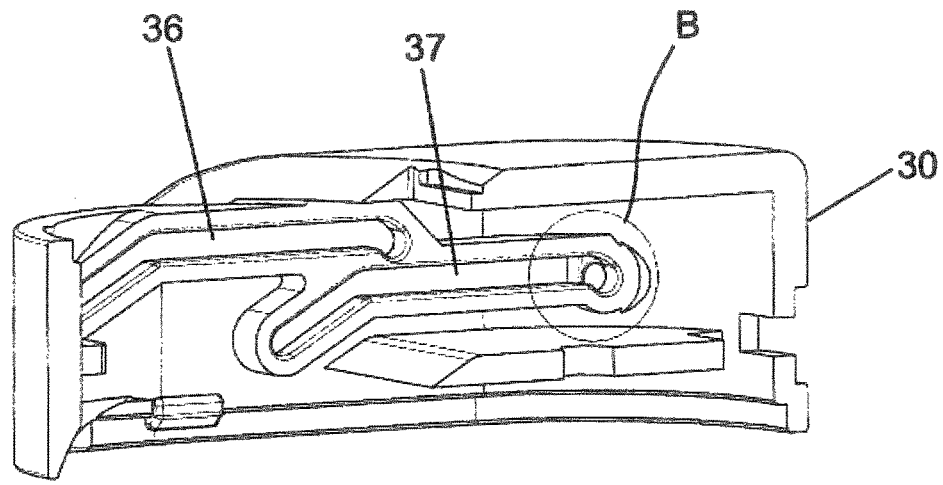
FIG. 16 is a detailed cross-sectional view of the pharmaceutical injection device in FIG. 1A.

As shown in FIG. 16, two slide grooves 36 and 37 are provided at the portions opposite the left and right slide pins 33 and 34 on the inner face side of the 30.

The slide grooves 36 guide the slide pins 33 when the cover 25 is slid in the outer peripheral direction (outside direction) of the injection needle mounting portion 2. The slide grooves 37 guide the slide pins 34 when the cover 25 is slid in the outer peripheral direction (outside direction) of the injection needle mounting portion 2.

When the slide pins 33 and 34 are mounted in these slide grooves 36 and 37, the fact that the substantially L-shaped arms 32 are formed from spring material is taken advantage of, and the substantially L-shaped arms 32 are elastically deformed to the inside (the direction in which the two substantially L-shaped arms 32 approach each other). This allows the slide pins 33 and 34 to be engaged with the slide grooves 36 and 37 by elastic recovery after the slide pins 33 and 34 have been disposed on the inside of the slide grooves 36 and 37.

That is, in this state, the slide pins 33 and 34 are slid and guided along the slide grooves 36 and 37. Consequently, the cover 25 is opened and shut with respect to the opening 31. As a result, the injection needle mounting portion 2 can be exposed from the opening 31, or covered by the cover 25.

Figure 17:
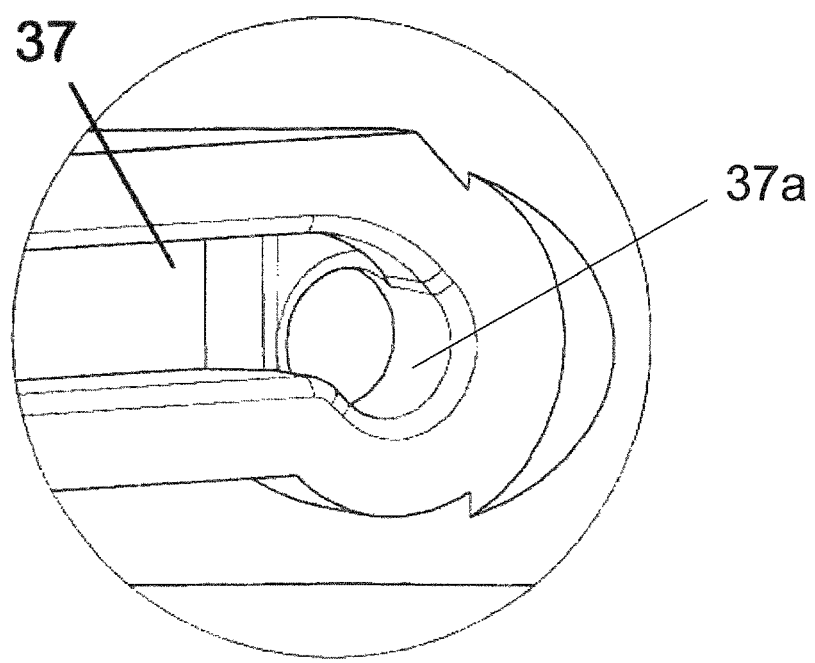
FIG. 17 is an enlarged view of the B portion in FIG. 16.

In this embodiment, the outer peripheral end side (the outer peripheral direction of the injection needle mounting portion 2) of the slide groove 37 is bent to the second end side (the power button 11 side) of the main body case 1, as shown in FIG. 17.

FIG. 17 is an enlarged view of the B portion in FIG. 16 (the circled portion, on the outer peripheral end side of the slide groove 37).

As discussed above, since the cover 25 is biased in the closing direction by the slide springs 35, the cover 25 will not accidentally come open.

When the cover 25 is pushed against the biasing force of the slide springs 35 (the operation to open the cover 25), the opening 31 is opened and the injection needle mounting portion 2 is exposed. The mounting of the injection needle 9 is performed in this state, as discussed above, but in this case since the cover 25 is biased in the closing direction by the slide springs 35 as mentioned above, something has to be done to keep the cover from being accidentally closed.

In view of this, in this embodiment, the configuration shown in FIG. 17 is employed so that the cover 25 will not be opened accidentally in a state in which the opening 31 is not covered by the cover 25 (when it is open). Specifically, the slide grooves 37 are provided with a bent part 37a at which the end on the side where the slide pins 34 move in a state of opening the cover 25 is bent to the second end side (the power button 11 side) of the main body case 1.

Consequently, the slide pins 34 are pulled against the bent parts 37a on the outer peripheral end side of the slide grooves 37 (the outer peripheral direction of the injection needle mounting portion 2) by the slide springs 35. This prevents accidental closing even if the cover 25 is pulled in the closing direction by the slide springs 35.

As shown in FIGS. 22 to 26, if the outside of the cover 25 (the opposite side from the injection needle mounting portion 2) is lifted after the pharmaceutical is injected and the injection needle 9 has been removed, the slide pins 34 will be lifted up from the bent parts 37a. As a result, the slide pins 34 are pulled by the slide springs 35, and the cover 25 can be closed from the state in FIG. 14 to that in FIG. 13.

As shown in FIGS. 5 to 12B, once the cover 25 is opened, as discussed above, the injection needle 9 is mounted to the injection needle mounting portion 2. After this, as shown in FIGS. 12A and 12B, the injection needle 9 is inserted into the skin 29 of the patient.

At this point, in this embodiment, as shown in FIGS. 12A and 12B, the surface of the cover 25 becomes the skin contact face at the outer peripheral position of the injection needle mounting portion 2.

That is, the injection needle 9 can be pushed by the proper amount (the proper depth in this case) into the skin 29 as long as the cover 25 is pressed far enough to hit the skin 29.

As discussed above, the distal end face on the injection needle 9 side of the stepped part 9a of the injection needle 9 is the same height as the front of the cover 25 (see FIG. 11). Accordingly, as long as the cover 25 is pressed against the skin 29, the injection needle 9 can be pushed the proper amount into the skin 29 (see FIGS. 12A and 12B).

When the pharmaceutical is being injected in the state in FIGS. 12A and 12B, the cover 25 has been pushed toward the main body case 1, so the slide pins 34 are pressed against the bent parts 37a on the outer peripheral end side (the outer peripheral direction of the injection needle mounting portion 2) of the slide grooves 37. Consequently, even if the cover 25 is pulled in the closing direction by the slide springs 35, the cover 25 can be prevented from accidentally closing.

Once this pharmaceutical injection is complete, as shown in FIGS. 22 to 25, the injection needle 9 is removed from the injection needle mounting portion 2 (which also serves as the distal end side of the pharmaceutical syringe 4).

At this point, the needle cover 28 is pushed into the injection needle 9, and then, as shown in FIG. 25, the needle cover 28 rotates, and the needle unit 26, including the injection needle 9, is removed from the injection needle mounting portion 2 (which also serves as the distal end side of the pharmaceutical syringe 4).

In the state in FIG. 25, if the outside of the main body case 1 (the opposite side from the injection needle mounting portion 2) is lifted, the slide pins 34 are lifted up from the above-mentioned bent parts 37a. As a result, the slide pins 34 are pulled by the slide springs 35, and the cover 25 can be closed from its state in FIG. 25 to that in FIG. 26.

In this state, the injection needle mounting portion 2 is covered by the cover 25, which is more sanitary.

Figure 30:
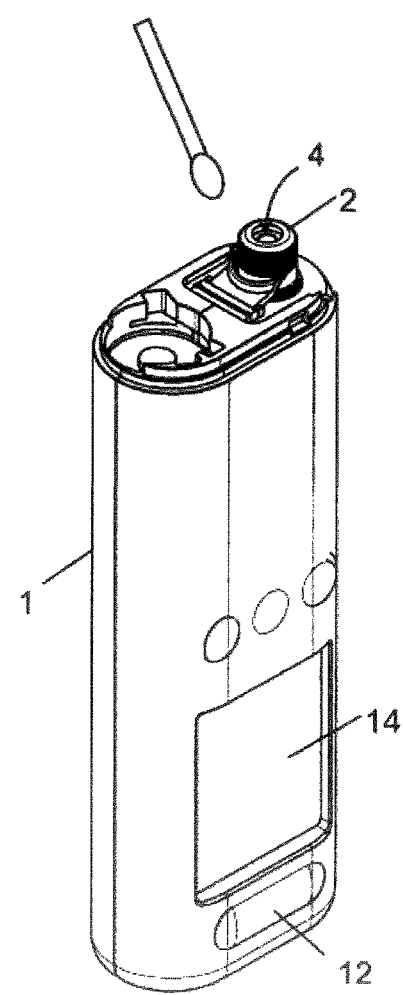
FIG. 30 is an oblique view of the usage state of the pharmaceutical injection device in FIG. 1A.
Figure 31:
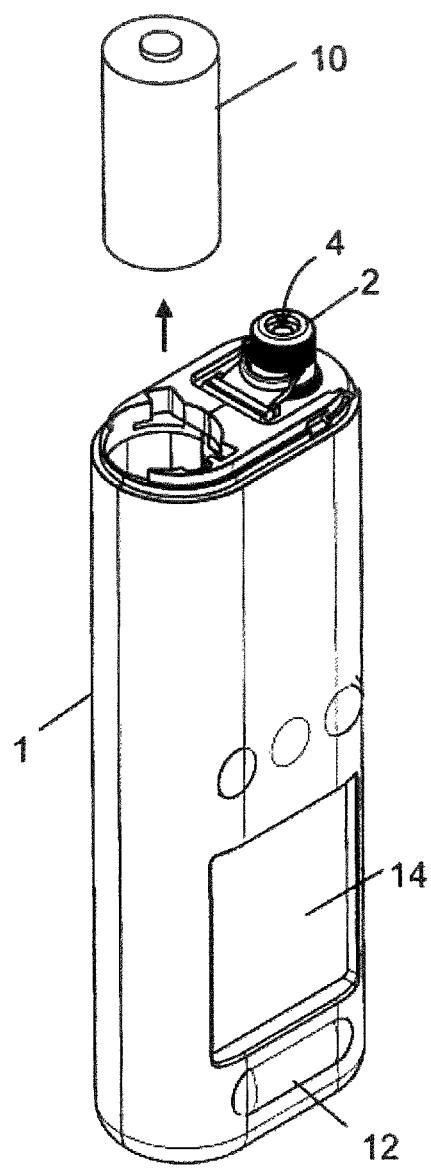
FIG. 31 is an oblique view of the usage state of the pharmaceutical injection device in FIG. 1A.

FIGS. 27 to 31 show the state when the cap 30 is removed from the main body case 1 (as shown in FIG. 30). When the injection needle mounting portion 2 is to be cleaned, the cap 30 can be removed from the main body case 1. Also, when the battery 10 in the main body case 1 is to be replaced, the cap 30 can be removed from the main body case 1 (as shown in FIGS. 27 to 31).

Figure 20:
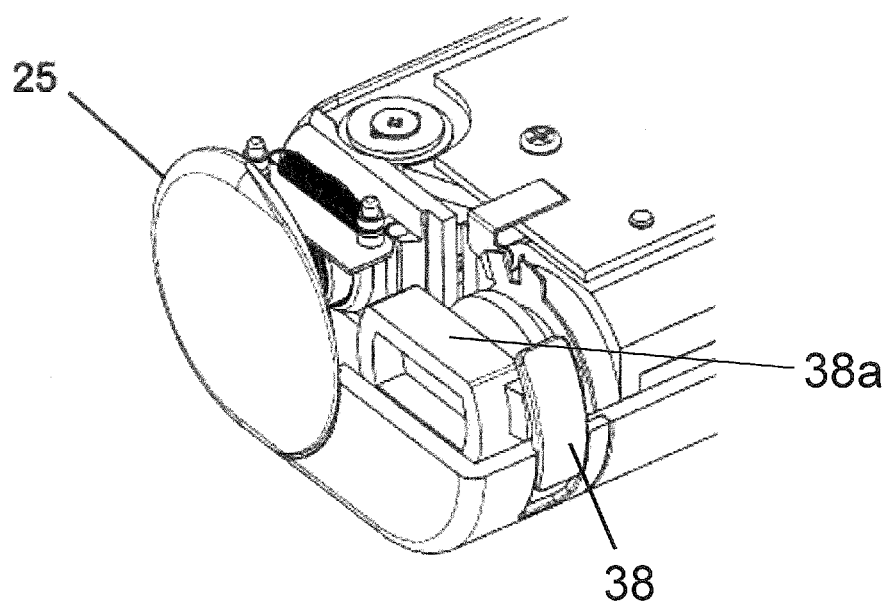
FIG. 20 is a detailed oblique view of the pharmaceutical injection device in FIG. 1A.
Figure 21:
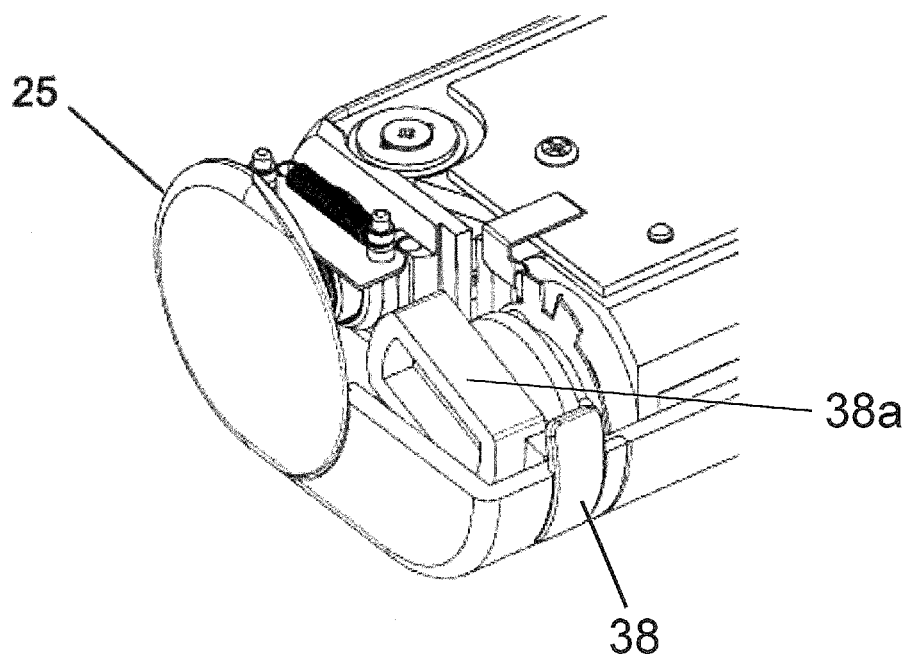
FIG. 21 is a detailed oblique view of the pharmaceutical injection device in FIG. 1A.
Figure 22:
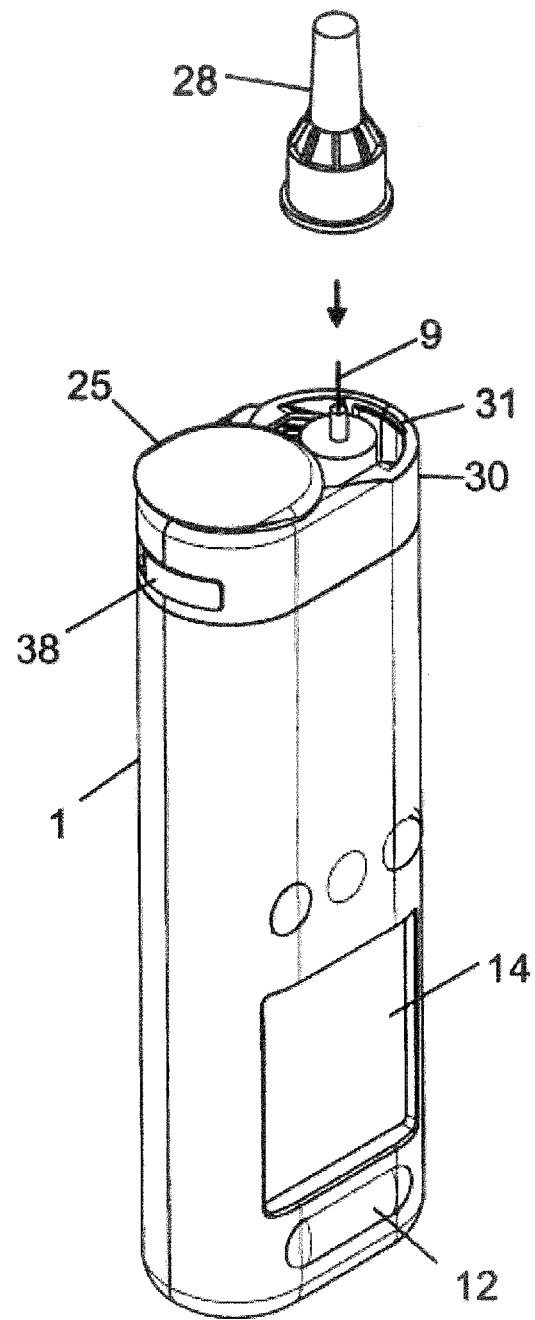
FIG. 22 is an oblique view of the usage state of the pharmaceutical injection device in FIG. 1A.
Figure 23:
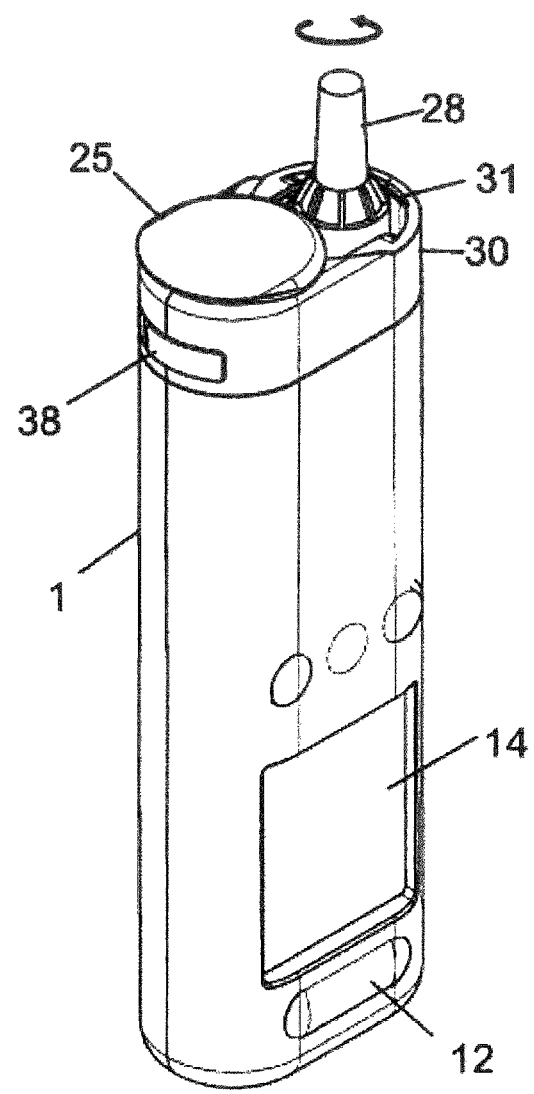
FIG. 23 is an oblique view of the usage state of the pharmaceutical injection device in FIG. 1A.
Figure 24:
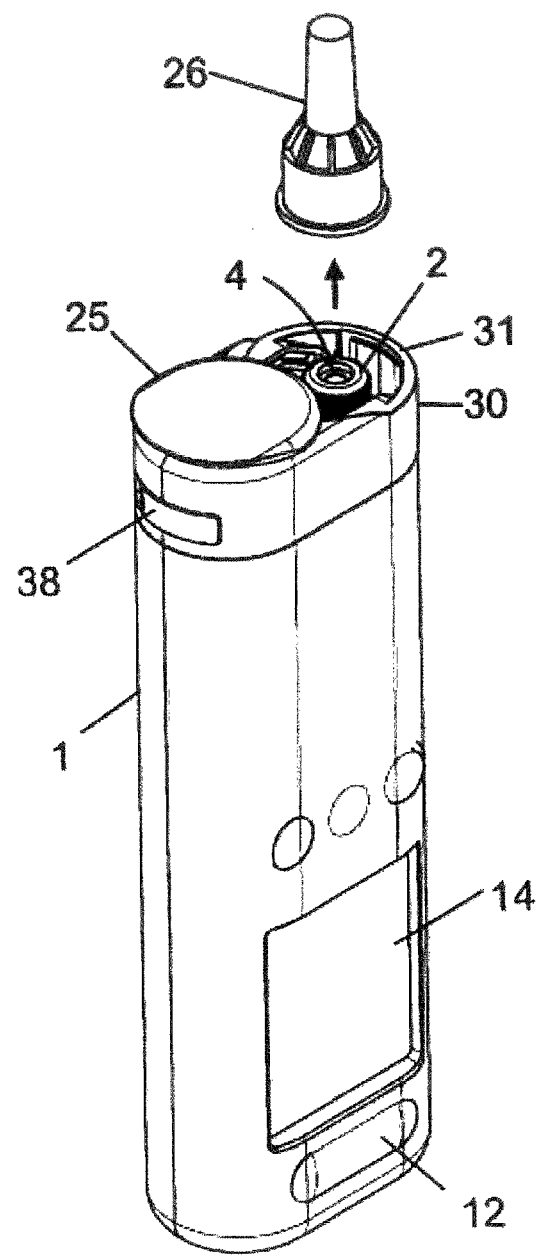
FIG. 24 is an oblique view of the usage state of the pharmaceutical injection device in FIG. 1A.

In the removal of the cap 30 from the main body case 1, when a lever 38 provided at the outer peripheral face of the cap 30 is operated, a locking mechanism 38a rotates in conjunction with the operation of the lever 38 to release the lock, as shown in FIGS. 20 and 21. More specifically, when the lever 38 is slid along the outer peripheral face of the cap 30, the locking mechanism 38a also rotates in conjunction with this, as shown in FIGS. 20 and 21. In the state shown in FIG. 21, because the lock by the locking mechanism 38a has been released, the cap 30 can be removed from the main body case 1.

Naturally, in the remounting of the cap 30 to the main body case 1, the locking mechanism should be used to ensure that the cap 30 and the main body case 1 are in a locked state.

As discussed above, in this embodiment, the cover 25, which covers the injection needle mounting portion 2 in an openable and closeable state while still attached to the main body case 1, is provided on the first end side of the main body case 1.

The front of the cover 25 becomes the skin contact face at the outer peripheral position of the injection needle mounting portion 2 when the opening is open.

That is, the cover 25 is always attached to the main body case 1 regardless of whether the opening is open or closed. Consequently, unlike with a conventional cover in which the injection needle mounting portion is exposed by removing the cover from the main body case, the cover 25 will never be lost, which makes the pharmaceutical injection device more convenient to use.

Also, during pharmaceutical injection, the cover 25 serves as the skin contact face at the outer peripheral position of the injection needle mounting portion 2, so the injection needle insertion depth during pharmaceutical injection can be stabilized. Also, since the operating orientation during pharmaceutical injection is also stable, the pharmaceutical injection device is more convenient to use in this respect as well.

The pharmaceutical injection device pertaining to another embodiment of the present invention will now be described through reference to FIGS. 32A to 32C.

The pharmaceutical injection device in this embodiment differs from previous embodiments in how the cover 25 is opened and closed.

Other than this difference, the members have basically the same function, etc., so they will be numbered the same as in previously discussed embodiments, and will not be described in detail again.

With the pharmaceutical injection device in this embodiment, as shown in FIGS. 32A to 32C, the configuration differs from other embodiments in that an opening and closing mechanism is employed which opens and closes the cover 25 by sliding it parallel to the upper end face of the cap 30 along horizontal grooves 30a formed in the cap 30.

More specifically, as shown in FIG. 32A and elsewhere, the two horizontal grooves 30a are formed parallel to the upper end face of the cap 30, on mutually opposite faces of the inner peripheral face of the cylindrical cap 30.

Similar to other embodiments, the cover 25 is attached to the upper end face of the cap 30 in a state in which it can be opened and closed with respect to the cap 30.

Consequently, as shown in FIGS. 32A to 32C, the side face portions of the cover 25 can be slid along the two horizontal grooves 30a to open and close the cover, making it easy to switch between a state in which the injection needle mounting portion 2 is exposed and a state in which it is covered by the cover 25, without having to remove the cover 25 from the main body case 1.

The pharmaceutical injection device pertaining to yet another embodiment of the present invention will now be described through reference to FIGS. 33A to 33C.

The pharmaceutical injection device in this embodiment differs from previous embodiments in how the cover 25 is opened and closed.

Other than this difference, the members have basically the same function, etc., so they will be numbered the same as in previous embodiments, and will not be described in detail again.

Specifically, with the pharmaceutical injection device in this embodiment, as shown in FIGS. 33A to 33C, the configuration differs from previous embodiments in that an opening and closing mechanism is employed which opens and closes the cover 25 by horizontally turning it around a shaft 25a.

More specifically, as shown in FIG. 33A and elsewhere, the shaft 25a, which is the turning center of the cover 25, is disposed along the lengthwise direction of the main body case 1.

Again in this embodiment, the cover 25 is attached to the upper end face of the cap 30 in a state in which it can be opened and closed with respect to the cap 30.

Consequently, as shown in FIGS. 33A to 33C, it is easy to switch between a state in which the injection needle mounting portion 2 is exposed and a state in which it is covered by the cover 25, by turning the cover 25 horizontally to open and close it, without having to remove it from the main body case 1.

As a result, the same effect as in previous embodiments can be obtained.

The pharmaceutical injection device pertaining to yet another embodiment of the present invention will now be described through reference to FIGS. 34A to 34C.

The pharmaceutical injection device in this embodiment differs from the configuration in other embodiments in how the cover 25 is opened and closed.

Other than this difference, the members have basically the same function, etc., so they will be numbered the same, and will not be described in detail again.

Figures 34A, 34B, 34C:
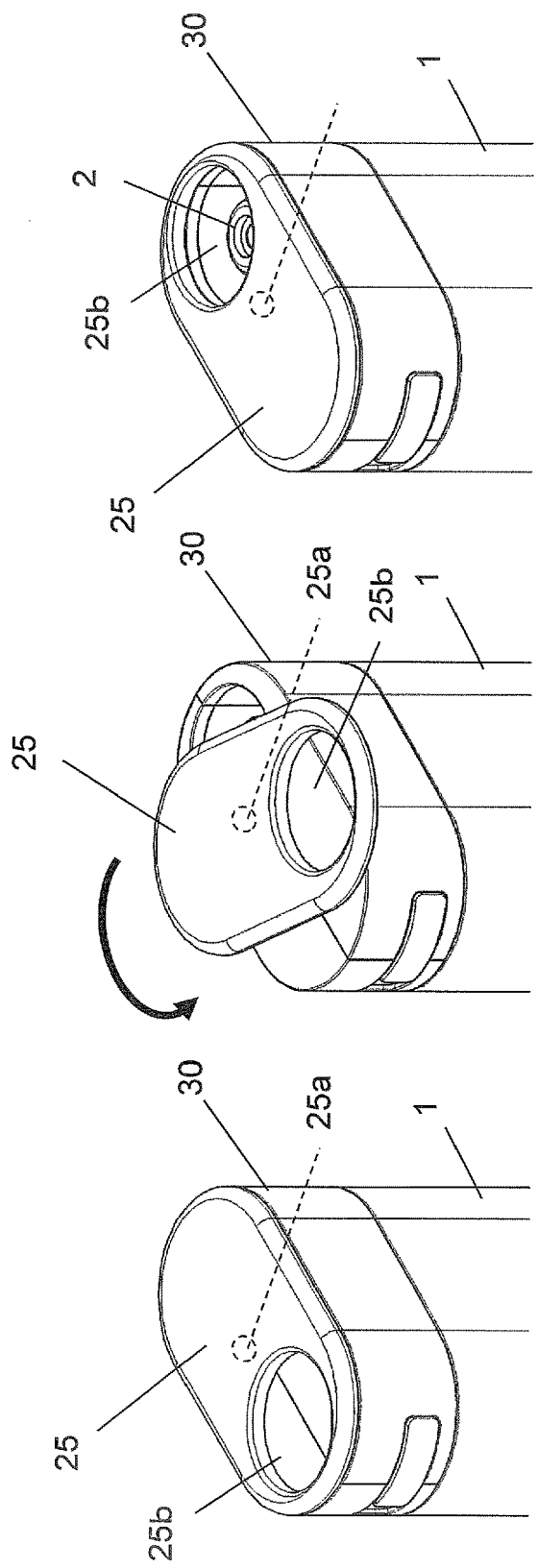
FIGS. 34A to 34C are oblique views of the configuration of the main components of the pharmaceutical injection device pertaining to yet another embodiment of the present invention.

Specifically, with the pharmaceutical injection device in this embodiment, as shown in FIGS. 34A to 34C, the configuration differs from that in previous embodiments in that an opening and closing mechanism is employed which switches the cover 25, in which an opening 25b is formed, between a state in which the injection needle mounting portion 2 is covered from the opening 25b (see FIG. 34A) and a state in which it is exposed (see FIG. 34C), by horizontally turning the cover 25 around the shaft 25a.

More specifically, as shown in FIG. 34A and elsewhere, the shaft 25a, which is the horizontal turning center of the cover 25, is disposed along the lengthwise direction of the main body case 1, in the approximate center of the upper end face of the cap 30. Also, the opening 25b formed in the cover 25 is formed large enough to expose the injection needle mounting portion 2 in a state in which the cover 25 has been horizontally turned and disposed over the injection needle mounting portion 2.

Again in this embodiment, the cover 25 is attached to the upper end face of the cap 30 in a state in which it can be opened and closed with respect to the cap 30.

Consequently, as shown in FIGS. 34A to 34C, it is easy to switch between a state in which the injection needle mounting portion 2 is exposed and a state in which it is covered by the cover 25, by turning the cover 25 horizontally to open and close it, without having to remove it from the main body case 1.

As a result, the same effect as in certain previous embodiments can be obtained.

The pharmaceutical injection device pertaining to yet another embodiment of the present invention will now be described through reference to FIGS. 35A to 35C.

The pharmaceutical injection device in this embodiment differs from the previous embodiments in how the cover 25 is opened and closed.

Other than this difference, the members have basically the same function, etc., so they will be numbered the same as in previous embodiments, and will not be described in detail again.

Specifically, with the pharmaceutical injection device in this embodiment, as shown in FIGS. 35A to 35C, the configuration differs from that in previous embodiments in that an opening and closing mechanism is employed which opens and closes the cover by opening and closing a part of the cover 25 that covers above the injection needle mounting portion 2, via a hinge member 39.

More specifically, as shown in FIG. 35A and elsewhere, the hinge member 39 for opening and closing the cover 25 is disposed in the approximate center of the upper end face of the cap 30.

Again in this embodiment, the cover 25 is attached to the upper end face of the cap 30 in a state in which it can be opened and closed with respect to the cap 30.

Consequently, as shown in FIGS. 35A to 35C, it is easy to switch between a state in which the injection needle mounting portion 2 is exposed and a state in which it is covered by the cover 25, by opening and closing the cover 25 via the hinge member 39, without having to remove it from the main body case 1.

As a result, the same effect as in previous embodiments can be obtained.

The pharmaceutical injection device pertaining to yet another embodiment of the present invention will now be described through reference to FIGS. 36A to 36C.

The pharmaceutical injection device in this embodiment differs from the configuration in previous embodiments in terms of how the cover 25 is opened and closed.

Other than this difference, the members have basically the same function, shape, etc., so they will be numbered the same, and will not be described in detail again.

Specifically, with the pharmaceutical injection device in this embodiment, as shown in FIG. 36B, when the pharmaceutical syringe mounting portion 3 has been opened in order to replace the pharmaceutical syringe 4, a stopper member 40 is disposed substantially in the horizontal direction, and at a height position that interferes with the L-shaped arms 32.

The stopper member 40 here rotates about a rotational shape 40a and is thereby disposed (moved) at heights that interfere and do not interfere with the L-shaped arms 32. This rotation of the stopper member 40 happens in conjunction with the operation to open up the pharmaceutical syringe mounting portion 3.

Consequently, movement of the L-shaped arms 32 in the opening and closing direction of the cover 25 can be restricted by the stopper member 40 so that the cover 25 will not accidentally come open during replacement of the pharmaceutical syringe 4, etc.

Meanwhile, when the pharmaceutical syringe mounting portion 3 is closed, as shown in FIG. 36A, the stopper member 40 is rotated downward and located lower than the L-shaped arms 32.

Consequently, movement of the L-shaped arms 32 in the opening and closing direction of the cover 25 is not restricted by the stopper member 40, allowing the cover 25 to be opened without any problem.

This prevents the cover 25 from accidentally coming open during pharmaceutical syringe replacement, so a pharmaceutical injection device can be obtained in which handling safety is further improved.

INDUSTRIAL APPLICABILITY

As discussed above, in certain embodiments of the present invention, the cover is always mounted to the main body case, so it will not be lost, and the device can be used more conveniently, and therefore embodiments of the present invention are expected to find wide application in the field of various kinds of pharmaceutical injection device, etc.

The invention claimed is:

1. A pharmaceutical injection device, comprising:
   a main body case having a first end side, the first end side having an injection needle mounting portion and an injection needle mounted to the injection needle mounting portion;
   a pharmaceutical syringe mounting portion that is provided inside the main body case and to which a pharmaceutical syringe is mounted;
   a piston that is provided movably with respect to the pharmaceutical syringe;
   a drive mechanism configured to drive the piston;
   a cover that covers the injection needle mounting portion in an opened or closed state wherein, in the opened state of the cover, the injection needle mounting portion is exposed to an outside while the cover is still attached to the first end side of the main body case;
   a stepped part that is formed on a rear side of the injection needle in a piercing direction; and
   an opening and closing mechanism for the cover, provided on the first end side of the main body case,
   wherein, in the opened state of the cover, a distal end face of the stepped part on an injection needle side is positioned at substantially a same height as a front of the cover, and a surface of the cover is a face that is configured to come into contact with a skin of a patient at an outer peripheral position of the injection needle mounting portion,
   wherein, in the closed state of the cover, the injection needle mounting portion is not exposed to the outside while the cover is still attached to the first end side of the main body case, and
   wherein the opening and closing mechanism includes:
   a first slide pin provided near the cover on an injection needle mounting portion side of the cover;
   a first slide groove configured to guide a sliding of the first slide pin in an outer peripheral direction of the injection needle mounting portion;
   a first slide spring configured to bias the first slide pin in a closing direction of the cover;
   a second slide pin provided on an outer peripheral side of the injection needle mounting portion;
   a second slide groove configured to guide a sliding of the second slide pin in the outer peripheral direction of the injection needle mounting portion; and
   a second slide spring that is in communication with the second slide pin and is configured to bias in the closing direction of the cover.

2. A pharmaceutical injection device, comprising:
   a main body case having a first end side, the first end side having an injection needle mounting portion and an injection needle mounted to the injection needle mounting portion;
   a pharmaceutical syringe mounting portion that is provided inside the main body case and to which a pharmaceutical syringe is mounted;
   a piston that is provided movably with respect to the pharmaceutical syringe;
   a drive mechanism configured to drive the piston;
   a cover that covers the injection needle mounting portion in an opened or closed state wherein, in the opened state of the cover, the injection needle mounting portion is exposed to an outside while the cover is still attached to the first end side of the main body case;
   wherein a surface of the cover is a face that is configured to come into contact with a skin of a patient at an outer peripheral position of the injection needle mounting portion in the opened state of the cover,
   wherein, in the closed state of the cover, the injection needle mounting portion is not exposed to the outside while the cover is still attached to the first end side of the main body case, and
   wherein, in the closed state of the cover, the cover is positioned distally closer to the injection needle mounting portion than when the cover is in the opened state; and
   an opening and closing mechanism for the cover, provided on the first end side of the main body case, the opening and closing mechanism including:
   a first slide pin provided near the cover on an injection needle mounting portion side of the cover;
   a first slide groove configured to guide a sliding of the first slide pin in an outer peripheral direction of the injection needle mounting portion
   a first slide spring configured to bias the first slide pin in a closing direction of the cover
   a second slide pin provided on an outer peripheral side of the injection needle mounting portion;
   a second slide groove configured to guide a sliding of the second slide pin in the outer peripheral direction of the injection needle mounting portion; and
   a second slide spring that is in communication with the second slide pin and is configured to bias in the closing direction of the cover.

* * * * *